United States Patent
Lavi et al.

(10) Patent No.: US 12,343,119 B2
(45) Date of Patent: Jul. 1, 2025

(54) AUTOMATED MEASUREMENT SYSTEM AND METHOD FOR CORONARY ARTERY DISEASE SCORING

(71) Applicant: CathWorks Ltd., Kfar Saba (IL)

(72) Inventors: Guy Lavi, Moshav Mishmeret (IL); Uri Merhav, Rechovot (IL)

(73) Assignee: CathWorks Ltd., Kfar Saba (IL)

( * ) Notice: Subject to any disclaimer, the term of this patent is extended or adjusted under 35 U.S.C. 154(b) by 0 days.

(21) Appl. No.: 18/336,847

(22) Filed: Jun. 16, 2023

(65) Prior Publication Data

US 2024/0099589 A1     Mar. 28, 2024

Related U.S. Application Data

(63) Continuation of application No. 17/700,899, filed on Mar. 22, 2022, now Pat. No. 11,707,196, which is a
(Continued)

(51) Int. Cl.
    *A61B 5/02*          (2006.01)
    *A61B 5/00*          (2006.01)
    (Continued)

(52) U.S. Cl.
    CPC ........ *A61B 5/02007* (2013.01); *A61B 5/1075* (2013.01); *A61B 5/7264* (2013.01);
    (Continued)

(58) Field of Classification Search
    CPC .......... A61B 2034/107; A61B 2576/00; A61B 34/10; A61B 5/02007; A61B 5/1075;
    (Continued)

(56) References Cited

U.S. PATENT DOCUMENTS

| | | |
|---|---|---|
| 5,150,292 A | 9/1992 | Hoffmann et al. |
| 5,638,823 A | 6/1997 | Akay et al. |
| (Continued) | | |

FOREIGN PATENT DOCUMENTS

| | | |
|---|---|---|
| AU | 2010298333 | 1/2012 |
| CN | 104282009 | 1/2015 |
| (Continued) | | |

OTHER PUBLICATIONS

Abraham et al., "Alternative routes in road networks", ACM Journal of Experimental Algorithmics, Association of Computing Machinery, vol. 18(1):1.3:2-1.3:17 (2013).
(Continued)

*Primary Examiner* — Manuchehr Rahmjoo
(74) *Attorney, Agent, or Firm* — Knobbe Martens Olson and Bear, LLP

(57) ABSTRACT

An automated measurement device and method for coronary artery disease scoring is disclosed. An example device includes a processor configured to obtain a computerized model of a plurality of vascular segments of a patient and create an unstenosed computerized model from the computerized model by virtually enlarging at least some locations of the vascular segments of the computerized model. The processor also determines vascular state scoring tool ("VSST") scores based on characteristics of vascular locations along the vascular segments. The processor further determines a severity of stenosis for the vascular locations based on comparisons of first blood flow parameter values at the vascular locations in the computerized model to corresponding second blood flow parameter values at the same vascular locations in the unstenosed computerized model. A user interface of the device displays the severity of stenosis in conjunction with the VSST scores for the vascular locations.

21 Claims, 10 Drawing Sheets

Related U.S. Application Data continuation of application No. 16/859,239, filed on Apr. 27, 2020, now Pat. No. 11,278,208, which is a continuation of application No. 16/291,916, filed on Mar. 4, 2019, now Pat. No. 10,631,737, which is a continuation of application No. 15/952,701, filed on Apr. 13, 2018, now Pat. No. 10,219,704, which is a continuation of application No. 14/437,205, filed as application No. PCT/IL2013/050869 on Oct. 24, 2013, now Pat. No. 9,943,233.

(60) Provisional application No. 61/717,732, filed on Oct. 24, 2012.

(51) Int. Cl.
*A61B 5/107* (2006.01)
*A61B 6/00* (2006.01)
*A61B 6/50* (2024.01)
*A61B 8/00* (2006.01)
*A61B 8/08* (2006.01)
*A61B 34/10* (2016.01)
*G06T 7/00* (2017.01)
*G16H 50/30* (2018.01)
*G16H 50/50* (2018.01)
*G16Z 99/00* (2019.01)

(52) U.S. Cl.
CPC ............ *A61B 5/7275* (2013.01); *A61B 6/504* (2013.01); *A61B 6/5217* (2013.01); *A61B 8/0891* (2013.01); *A61B 8/5223* (2013.01); *A61B 34/10* (2016.02); *G06T 7/0012* (2013.01); *G16H 50/30* (2018.01); *G16H 50/50* (2018.01); *G16Z 99/00* (2019.02); *A61B 2034/107* (2016.02); *A61B 2576/00* (2013.01); *G06T 2207/10072* (2013.01); *G06T 2207/30101* (2013.01)

(58) Field of Classification Search
CPC ..... A61B 5/7264; A61B 5/7275; A61B 6/504; A61B 6/5217; A61B 8/0891; A61B 8/5223; G06T 2207/10072; G06T 2207/30101; G06T 7/0012; G16H 50/30; G16H 50/50; G16Z 99/00
See application file for complete search history.

(56) References Cited

U.S. PATENT DOCUMENTS

| | | | |
|---|---|---|---|
| 6,047,080 A | | 4/2000 | Chen et al. |
| 6,186,948 B1 | * | 2/2001 | Kamiyama ............ A61B 8/13 600/443 |
| 6,236,878 B1 | | 5/2001 | Taylor et al. |
| 6,501,848 B1 | | 12/2002 | Carroll et al. |
| 6,842,638 B1 | | 1/2005 | Suri et al. |
| 7,113,623 B2 | | 9/2006 | Chen et al. |
| 7,339,585 B2 | | 3/2008 | Verstraelen et al. |
| 7,369,691 B2 | | 5/2008 | Kondo et al. |
| 7,574,026 B2 | | 8/2009 | Rasche et al. |
| 7,657,299 B2 | | 2/2010 | Huizenga et al. |
| 7,693,315 B2 | | 4/2010 | Krishnan et al. |
| 7,738,626 B2 | | 6/2010 | Weese et al. |
| 7,808,503 B2 | | 10/2010 | Duluk, Jr. et al. |
| 7,860,283 B2 | | 12/2010 | Begelman et al. |
| 7,864,997 B2 | | 1/2011 | Aben |
| 7,912,260 B2 | | 3/2011 | Breeuwer et al. |
| 7,970,187 B2 | | 6/2011 | Puts et al. |
| 7,983,459 B2 | | 7/2011 | Begelman et al. |
| 8,073,224 B2 | | 12/2011 | Strobel et al. |
| 8,086,000 B2 | | 12/2011 | Weijers et al. |
| 8,090,164 B2 | | 1/2012 | Bullitt et al. |
| 8,155,411 B2 | | 4/2012 | Hof et al. |
| 8,298,147 B2 | | 10/2012 | Huennekens et al. |
| 8,311,748 B2 | | 11/2012 | Taylor et al. |
| 8,311,750 B2 | | 11/2012 | Taylor |
| 8,315,812 B2 | | 11/2012 | Taylor |
| 8,321,150 B2 | | 11/2012 | Taylor |
| 8,331,314 B2 | | 12/2012 | Quiang et al. |
| 8,496,594 B2 | | 7/2013 | Taylor et al. |
| 8,523,779 B2 | | 9/2013 | Taylor et al. |
| 8,548,778 B1 | | 10/2013 | Hart et al. |
| 8,554,490 B2 | | 10/2013 | Tang et al. |
| 8,560,968 B1 | | 10/2013 | Nair |
| 8,715,184 B2 | | 5/2014 | Lazebnik |
| 8,768,669 B1 | | 7/2014 | Hart et al. |
| 8,771,195 B2 | | 7/2014 | Kim et al. |
| 8,787,641 B2 | | 7/2014 | Hof et al. |
| 8,812,246 B2 | | 8/2014 | Taylor |
| 8,824,752 B1 | | 9/2014 | Fonte et al. |
| 8,861,820 B2 | | 10/2014 | Fonte et al. |
| 8,934,686 B2 | | 1/2015 | Ostrovsky-Berman et al. |
| 8,970,578 B2 | | 3/2015 | Voros et al. |
| 9,008,405 B2 | | 4/2015 | Fonte et al. |
| 9,042,613 B2 | | 5/2015 | Spilker et al. |
| 9,078,564 B2 | | 7/2015 | Taylor |
| 9,129,418 B2 | | 9/2015 | Schormans et al. |
| 9,138,147 B2 | | 9/2015 | Schmitt et al. |
| 9,189,600 B2 | | 11/2015 | Spilker et al. |
| 9,256,936 B2 | | 2/2016 | Jacobs et al. |
| 9,314,584 B1 | | 4/2016 | Riley et al. |
| 9,375,191 B2 | | 6/2016 | Verstraelen et al. |
| 9,406,141 B2 | | 8/2016 | Kelm et al. |
| 9,430,827 B2 | | 8/2016 | Kelm et al. |
| 9,466,117 B2 | | 10/2016 | Habets et al. |
| 9,471,999 B2 | | 10/2016 | Ishii et al. |
| 9,572,495 B2 | | 2/2017 | Schmitt et al. |
| 9,576,360 B2 | | 2/2017 | Schormans et al. |
| 9,615,755 B2 | | 4/2017 | Riley et al. |
| 9,706,925 B2 | | 7/2017 | Taylor |
| 9,743,835 B2 | | 8/2017 | Taylor |
| 9,786,068 B2 | | 10/2017 | Ishii et al. |
| 9,801,689 B2 | | 10/2017 | Taylor |
| 9,805,465 B2 | | 10/2017 | Kyriakou |
| 9,814,433 B2 | | 11/2017 | Benishti et al. |
| 9,858,387 B2 | | 1/2018 | Lavi et al. |
| 9,870,634 B2 | | 1/2018 | Grady et al. |
| 9,940,736 B2 | | 4/2018 | Ishii et al. |
| 9,943,233 B2 | | 4/2018 | Lavi et al. |
| 9,968,256 B2 | | 5/2018 | Taokowsky et al. |
| 9,977,869 B2 | | 5/2018 | Lavi et al. |
| 9,999,361 B2 | | 6/2018 | Sharma et al. |
| 10,141,074 B2 | | 11/2018 | Lavi et al. |
| 10,159,529 B2 | | 12/2018 | Taylor |
| 10,210,956 B2 | | 2/2019 | Lavi et al. |
| 10,219,704 B2 | | 3/2019 | Lavi et al. |
| 10,342,442 B2 | | 7/2019 | Hattangadi et al. |
| 10,354,744 B2 | | 7/2019 | Sharma et al. |
| 10,373,700 B2 | | 8/2019 | Sharma et al. |
| 10,395,774 B2 | | 8/2019 | Lavi et al. |
| 10,424,063 B2 | | 9/2019 | Lavi et al. |
| 10,456,094 B2 | | 10/2019 | Fonte et al. |
| 10,470,730 B2 | | 11/2019 | Benishti et al. |
| 10,559,388 B2 | | 2/2020 | Lavi et al. |
| 10,595,807 B2 | | 3/2020 | Lavi et al. |
| 10,631,737 B2 | | 4/2020 | Lavi et al. |
| 10,682,180 B2 | | 6/2020 | Taylor |
| 10,702,339 B2 | | 7/2020 | Taylor |
| 10,748,285 B2 | | 8/2020 | Igarashi et al. |
| 11,081,237 B2 | | 8/2021 | Lavi et al. |
| 11,083,524 B2 | | 8/2021 | Taylor |
| 11,087,884 B2 | | 8/2021 | Sankaran et al. |
| 11,090,118 B2 | | 8/2021 | Taylor |
| 11,116,575 B2 | | 9/2021 | Taylor |
| 11,138,733 B2 | | 10/2021 | Lavi et al. |
| 11,185,368 B2 | | 11/2021 | Spilker et al. |
| 11,202,612 B2 | | 12/2021 | Sakaguchi |
| 11,272,845 B2 | | 3/2022 | Cheline et al. |
| 11,278,208 B2 | | 3/2022 | Lavi et al. |
| 11,295,864 B2 | | 4/2022 | Benishti et al. |
| 11,298,187 B2 | | 4/2022 | Taylor |
| 11,304,665 B2 | | 4/2022 | Sharma et al. |

(56) References Cited

U.S. PATENT DOCUMENTS

| | | |
|---|---|---|
| 11,382,569 B2 | 7/2022 | Grady et al. |
| 11,406,337 B2 | 8/2022 | Lavi et al. |
| 11,423,532 B2 | 8/2022 | Takahashi et al. |
| 11,538,161 B2 | 12/2022 | Wang et al. |
| 11,557,069 B2 | 1/2023 | Senzig et al. |
| 11,564,746 B2 | 1/2023 | Spilker et al. |
| 11,576,626 B2 | 2/2023 | Fonte et al. |
| 11,583,340 B2 | 2/2023 | Taylor |
| 11,615,894 B2 | 3/2023 | Lavi et al. |
| 11,666,236 B2 | 6/2023 | Lavi et al. |
| 11,707,196 B2 | 7/2023 | Lavi et al. |
| 11,728,037 B2 | 8/2023 | Lavi et al. |
| 11,793,575 B2 | 10/2023 | Taylor |
| 11,810,661 B2 | 11/2023 | Barley et al. |
| 11,816,837 B2 | 11/2023 | Lavi et al. |
| 11,826,106 B2 | 11/2023 | Hart et al. |
| 12,016,635 B2 | 6/2024 | Taylor |
| 12,079,994 B2 | 9/2024 | Lavi et al. |
| 12,094,112 B2 | 9/2024 | Gulsun et al. |
| 2003/0105401 A1 | 6/2003 | Jago et al. |
| 2004/0019264 A1 | 1/2004 | Suurmond et al. |
| 2004/0066958 A1 | 4/2004 | Chen et al. |
| 2005/0041842 A1 | 2/2005 | Frakes et al. |
| 2005/0043614 A1 | 2/2005 | Huizenga et al. |
| 2005/0249327 A1 | 11/2005 | Wink et al. |
| 2005/0272992 A1 | 12/2005 | O'Donnell et al. |
| 2006/0036167 A1 | 2/2006 | Shina |
| 2006/0074285 A1 | 4/2006 | Zarkh et al. |
| 2006/0084862 A1 | 4/2006 | Suurmond et al. |
| 2007/0031019 A1 | 2/2007 | Lesage et al. |
| 2007/0167833 A1 | 7/2007 | Redel et al. |
| 2008/0020362 A1 | 1/2008 | Cotin et al. |
| 2008/0187199 A1 | 8/2008 | Gulsun et al. |
| 2008/0205722 A1 | 8/2008 | Schaefer et al. |
| 2009/0016483 A1 | 1/2009 | Kawasaki et al. |
| 2009/0016587 A1 | 1/2009 | Strobel et al. |
| 2009/0171321 A1 | 7/2009 | Callaghan |
| 2009/0299640 A1 | 12/2009 | Ellis et al. |
| 2009/0312648 A1 | 12/2009 | Zhang et al. |
| 2010/0010428 A1 | 1/2010 | Yu et al. |
| 2010/0017171 A1 | 1/2010 | Spilker et al. |
| 2010/0021025 A1 | 1/2010 | Hof et al. |
| 2010/0067760 A1 | 3/2010 | Zhang et al. |
| 2010/0125197 A1 | 5/2010 | Fishel |
| 2010/0160764 A1 | 6/2010 | Steinberg et al. |
| 2010/0160773 A1 | 6/2010 | Cohen et al. |
| 2010/0220917 A1 | 9/2010 | Steinberg et al. |
| 2010/0296709 A1 | 11/2010 | Ostrovsky-Berman et al. |
| 2010/0298719 A1 | 11/2010 | Thrysoe et al. |
| 2011/0015530 A1 | 1/2011 | Misawa |
| 2011/0096907 A1 | 4/2011 | Mohamed |
| 2011/0134433 A1 | 6/2011 | Yamada |
| 2011/0135175 A1 | 6/2011 | Ostrovsky-Berman et al. |
| 2011/0142313 A1 | 6/2011 | Pack et al. |
| 2011/0182492 A1 | 7/2011 | Grass et al. |
| 2012/0014574 A1 | 1/2012 | Ferschel et al. |
| 2012/0041318 A1 | 2/2012 | Taylor |
| 2012/0041739 A1 | 2/2012 | Taylor |
| 2012/0053918 A1 | 3/2012 | Taylor |
| 2012/0053919 A1 | 3/2012 | Taylor |
| 2012/0053921 A1 | 3/2012 | Taylor |
| 2012/0059246 A1 | 3/2012 | Taylor |
| 2012/0059249 A1 | 3/2012 | Verard et al. |
| 2012/0062841 A1 | 3/2012 | Stetson et al. |
| 2012/0072190 A1 | 3/2012 | Sharma et al. |
| 2012/0075284 A1 | 3/2012 | Rivers et al. |
| 2012/0150048 A1* | 6/2012 | Kang ............... G06T 7/149 600/481 |
| 2012/0177275 A1 | 7/2012 | Suri |
| 2012/0230565 A1 | 9/2012 | Steinberg et al. |
| 2012/0236032 A1 | 9/2012 | Arvidsson |
| 2012/0243761 A1 | 9/2012 | Senzig et al. |
| 2013/0054214 A1* | 2/2013 | Taylor ............... A61B 5/7278 702/19 |
| 2013/0060133 A1 | 3/2013 | Kassab et al. |
| 2013/0094745 A1 | 4/2013 | Sundar |
| 2013/0158476 A1 | 6/2013 | Olson |
| 2013/0182936 A1 | 7/2013 | Yoshihara et al. |
| 2013/0226003 A1 | 8/2013 | Edic et al. |
| 2013/0229621 A1 | 9/2013 | Stetson et al. |
| 2013/0324842 A1 | 12/2013 | Mittal et al. |
| 2014/0005535 A1 | 1/2014 | Edic et al. |
| 2014/0046642 A1 | 2/2014 | Hart et al. |
| 2014/0086461 A1 | 3/2014 | Yao et al. |
| 2014/0094693 A1 | 4/2014 | Cohen et al. |
| 2014/0094697 A1 | 4/2014 | Petroff et al. |
| 2014/0100451 A1 | 4/2014 | Tolkowsky et al. |
| 2014/0121513 A1 | 5/2014 | Tolkowsky et al. |
| 2014/0142398 A1 | 5/2014 | Patil et al. |
| 2014/0200867 A1 | 7/2014 | Lavi et al. |
| 2014/0249790 A1 | 9/2014 | Spilker et al. |
| 2014/0303495 A1 | 10/2014 | Fonte et al. |
| 2014/0371578 A1 | 12/2014 | Auvray et al. |
| 2015/0201897 A1 | 7/2015 | Kyriakou |
| 2015/0213600 A1 | 7/2015 | Kyriakou |
| 2015/0265162 A1 | 9/2015 | Lavi et al. |
| 2015/0265222 A1 | 9/2015 | Sakaguchi |
| 2015/0335304 A1 | 11/2015 | Lavi et al. |
| 2015/0339847 A1 | 11/2015 | Benishti et al. |
| 2015/0342551 A1 | 12/2015 | Lavi et al. |
| 2016/0007945 A1 | 1/2016 | Taylor |
| 2016/0015349 A1* | 1/2016 | Ohuchi ............ A61B 5/7425 600/407 |
| 2016/0073928 A1 | 3/2016 | Soper et al. |
| 2016/0110866 A1 | 4/2016 | Taylor |
| 2016/0110867 A1 | 4/2016 | Taylor |
| 2016/0128661 A1 | 5/2016 | Taylor |
| 2016/0247279 A1 | 8/2016 | Lavi et al. |
| 2018/0102189 A1* | 4/2018 | Hosoi ................ G16H 40/20 |
| 2018/0268941 A1 | 9/2018 | Lavi et al. |
| 2018/0344174 A9 | 12/2018 | Schmitt et al. |
| 2019/0180880 A1 | 6/2019 | Lavi et al. |
| 2020/0126229 A1 | 4/2020 | Lavi et al. |
| 2020/0349708 A1 | 11/2020 | Igarashi et al. |
| 2021/0244293 A1* | 8/2021 | Belleville ............ A61B 5/0215 |
| 2021/0244475 A1 | 8/2021 | Taylor |
| 2021/0267690 A1 | 9/2021 | Taylor |
| 2021/0282860 A1 | 9/2021 | Taylor |
| 2021/0358634 A1 | 11/2021 | Sankaran et al. |
| 2021/0375474 A1 | 12/2021 | Lavi et al. |
| 2022/0028080 A1 | 1/2022 | Lavi et al. |
| 2022/0079563 A1 | 3/2022 | Kemp |
| 2022/0087544 A1 | 3/2022 | Schmitt et al. |
| 2022/0110687 A1 | 4/2022 | Spilker et al. |
| 2022/0211280 A1 | 7/2022 | Lavi et al. |
| 2022/0230312 A1 | 7/2022 | Choi et al. |
| 2022/0233081 A1 | 7/2022 | Cheline et al. |
| 2022/0277447 A1 | 9/2022 | Wang et al. |
| 2023/0084748 A1 | 3/2023 | Lavi et al. |
| 2023/0142219 A1* | 5/2023 | Makino ............... G16H 30/40 382/128 |
| 2023/0148977 A1 | 5/2023 | Fonte et al. |
| 2023/0282365 A1 | 9/2023 | Lavi et al. |
| 2023/0298176 A1 | 9/2023 | Choi et al. |
| 2023/0352152 A1 | 11/2023 | Grady et al. |
| 2024/0050159 A1 | 2/2024 | Hart et al. |
| 2024/0130796 A1 | 4/2024 | Song et al. |
| 2024/0153087 A1 | 5/2024 | Lavi et al. |
| 2024/0315777 A1 | 9/2024 | Choi et al. |

FOREIGN PATENT DOCUMENTS

| | | |
|---|---|---|
| EP | 1396274 | 3/2004 |
| EP | 2163272 | 3/2010 |
| EP | 2633815 A1 | 9/2013 |
| EP | 2779907 | 9/2014 |
| EP | 2873371 | 5/2015 |
| EP | 2633815 B1 | 6/2017 |
| EP | 3363350 | 8/2018 |
| EP | 3460688 | 3/2019 |
| EP | 2776960 | 9/2021 |
| EP | 3534372 | 9/2021 |
| EP | 3282380 | 11/2021 |
| EP | 3282381 | 11/2021 |

(56) References Cited

FOREIGN PATENT DOCUMENTS

| | | |
|---|---|---|
| EP | 3903672 | 11/2021 |
| EP | 3664026 | 2/2022 |
| EP | 3076854 | 4/2022 |
| EP | 3979259 | 4/2022 |
| EP | 3258446 | 5/2022 |
| EP | 3298959 | 9/2022 |
| EP | 3846176 | 9/2024 |
| JP | H08-131429 | 5/1996 |
| JP | 2003-508152 | 3/2003 |
| JP | 2003-514600 | 4/2003 |
| JP | 2004-243117 | 9/2004 |
| JP | 2007-502644 | 2/2007 |
| JP | 2007-325920 | 12/2007 |
| JP | 4177217 B2 | 11/2008 |
| JP | 2010-042247 | 2/2010 |
| JP | 2011-212314 | 10/2011 |
| JP | 2013-090799 | 5/2013 |
| JP | 2010-505493 | 7/2013 |
| JP | 2013-534154 | 9/2013 |
| JP | 2014-064915 | 4/2014 |
| JP | 2014-128631 | 7/2014 |
| JP | 2015-527901 | 9/2015 |
| WO | WO 2001/21057 | 3/2001 |
| WO | WO 2007/066249 | 6/2007 |
| WO | WO 2010/033971 | 3/2010 |
| WO | WO 2011/038044 | 3/2011 |
| WO | WO 2011/039685 | 4/2011 |
| WO | WO 2012/021037 | 2/2012 |
| WO | WO 2012/021307 | 2/2012 |
| WO | WO 2012/043498 | 4/2012 |
| WO | WO 2012/173697 | 12/2012 |
| WO | WO 2013/102880 | 7/2013 |
| WO | WO 2014/027692 | 2/2014 |
| WO | WO 2014/064702 | 5/2014 |
| WO | WO 2014/111927 | 7/2014 |
| WO | WO 2014/111929 | 7/2014 |
| WO | WO 2014/111930 | 7/2014 |
| WO | WO 2015/059706 | 4/2015 |

OTHER PUBLICATIONS

Andriotis et al., "A new method of three-dimensional coronary artery reconstruction from X-Ray angiography: Validation against a virtual phantom and multislice computed tomography", Catheterization and Cardiovascular Interventions, vol. 71:28-43 (2008).

Barnea, "Model-based estimation of coronary vessel diameter in angiographic images", Proceedings of the 20th Annual International Conference of the IEEE Engineering in Medicine and Biology Society, vol. 20:513-516 (1998).

Barratt et al., "Reconstruction and quantification of the carotid artery bifurcation from 3-D ultrasound images", IEEE Transactions on Medical Imaging, vol. 23(5):567-583 (2004).

Bullitt et al., "Determining malignancy of brain tumors by analysis of vessel shape", Medical Image Computing and Computer-Assisted Intervention, MICCAI 2004 Conference Proceedings, Lecture notes in Computer Science, LNCS, 3217:645-653.

Caiati et al., "New noninvasive method for coronary flow reserve assessment: Contrast-enhanced transthoracic second harmonic echo doppler", Circulation, vol. 99:771-778 (1999).

Caiati et al., "Detection, location, and severity assessment of left anterior descneding coronary artery stenoses by means of contrast-enhanced transthoracic harmonic echo dopper", European Heart Journal, vol. 30:1797-1806 (2009).

Chung, "Image segmentation methods for detecting blood vessels in angiography", 2006 9th International Conference on Control, Automation, Robotics and Vision, Singapore, pp. 1-6 (2006).

Dickie et al., "Live-vessel: interactive vascular image segmentation with simultaneous extraction of optimal medial and boundary paths", Technical Report TR 2009-23, School of Computing Science, Simon Fraser University, Burnaby, BC, Canada, Nov. 2009.

Frangi et al., "Multiscale vessel and enhancement filtering", Medical Image Computing and Computer-Assisted Intervention, MICCA '98 Lecture Notes in Computer Science, vol. 1496:130-137 (1998).

Fraz, "Blood vessel segmentation methodologies, in retinal images—a survey", Computer Methods and Programs in Biomedicine, vol. 108:407-433 (2012).

Fusejima, "Noninvasive measurement of coronary artery blood flow using combined two-dimensional and doppler echocardiography", JACC vol. 10(5):1024-1031 (1987).

Hawkes et al., "Validation of vol. blood flow measurements using three-dimensional distance-concentration functions detived from digital X-Ray angiograms", Investigative Radiology, vol. 29(4):434-442 (1994).

Hoffmann et al., "Determination of instantaneous and average blood flow rates from digital angiograms of vessel phantoms using distance-density curves", Investigative Radiology, vol. 26(3):207-212 (1991).

Holdsworth et al., "Quantitative angiographic blood-flow measurement using pulsed intra-arterial injection", Medical Physics, vol. 26(10):2168-2175 (1999).

Huo et al., "Intraspecific scaling laws of vascular trees", J.R. Soc. Interface vol. 9:190-200 (2012).

Janssen et al., "New approaches for the assessment of vessel sizes in quantitative (cardio-)vascular X-ray analysis", Int J Cardiovasc Imaging vol. 26:259-271 (2010).

Jiang et al., "Vascular tree reconstruction by minimizing a physiological functional cost", 2010 IEEE Computer Society Conference on Computer Vision and Pattern Recognition-workshops, San Francisco, CA, pp. 178-185, doi: 10.1109/CVPRW.2010.5543593.

Kappetein et al, "Current percutaneous coronary intervention and coronary artery bypass grafting practices for three-vessel and left main coronary artery disease: Insights from the SYNTAX run-in phase", European Journal of Cardio-Thoracic Surgery, vol. 29:486-491 (2010).

Kass et al., "Snakes: active contour models", Int. J. Comput. Vis. vol. 1:321-331 (1987).

Kirkeeide, "Coronary obstructions, morphology and physiologic significance", Quantitative Coronary Arteriography, Chap. 11:229-244 (1991).

Lethen et al., "Validation of noninvasive assessment of coronary flow velocity reserve in the right coronary artery—A comparison of transthoracic echocardiographic results with intracoronary doppler flow wire measurements", European Heart Journal, vol. 24:1567-1575 (2003).

Li et al, "Minimization of region-scalable fitting energy for image segmentation", in IEEE Transactions on Image Processing, vol. 17(10):1940-1949 (2008).

Meimoun et al., "Non-invasive assessment of coronary flow and coronary flow reserve by transthoracic doppler echocardiography: a magic tool for the real world", European Journal of Echocardiography, vol. 9:449-457 (2008).

Mercer-Rosa et al., "Illustration of the additional value of real-time 3-dimensional echocardiography to conventional transthoracic and transesophageal 2-dimensional echocardiography in imaging muscular ventricular septal defects: does this have any impact on individual patient treatment", Journal of the American Society of Echocardiography, vol. 19(12):1511-1519 (2006).

Molloi et al., "Quantification of fractional flow reserve using angiographic image data", World Congress on Medical Physics and Biomedical Engineering, Munich, Germany, Sep. 7-12, 2009.

Molloi et al., "Estimation of coronary artery hyperemic blood flow based on arterial lumen vol. using angiographic images", Int J Cardiovasc Imaging, vol. 28:1-11 (2012).

Ng et al., "Novel QCA methodologies and angiographic scores", Int J Cardiovasc Imaging vol. 27:157-165 (2011).

Pellot et al., "A 3D reconstruction of vascular structures from two X-Ray angiograms using an adapted simulated annealing algorithm", IEEE Transactions of Medical Imaging, vol. 13(1):48-60 (1994).

Pinho et al., "Assessment and stenting of tracheal stenosis using deformable shape models", Medical Image Analysis, vol. 15(2):250-266 (2010).

(56) References Cited

OTHER PUBLICATIONS

Polytimi et al., "Close to transplant renal artery stenosis and percutaneous transluminal treatment", Journal of Transplantation, vol. 2011, 7 pages (2011).
Sarwal et al., "3-D reconstruction of coronary arteries", Proceedings of the 16th Annual Intl. Conference of the IEEE Engineering in Medicine and Biology Society, Engineering Advances: New Opportunities for Biomedical Engineers, Nov. 3, 1994, pp. 504-505.
Sato et al., "A viewpoint determination system for stenosis diagnosis and quantification in coronary angiogrphic image acquisition", IEEE Transactions on Medical Imaging, vol. 17(1):121-137 (1998).
Seifalian et al., "A new algorithm for deriving pulsatile blood flow waveforms tested using simulated dynamic angiographic data", Neuroradiology, vol. 31:263-269 (1989).
Seifalian et al., "Blood flow measurements using 3D distance-concentration functions derived from digital x-ray angiograms", Cardiovascular Imaging, Chap. 33:425-442 (1996).
Seifalian et al., "Validation of a quantitative radiographic technique to estimate pulsatile blood flow waveforms using digital subtraction angiographic data", Journal of Biomedical Engineering, vol. 13(3):225-233 (1991).
Shang et al., "Vascular active contour for vessel tree segmentation", in IEEE Transactions on Biomedical Engineering, vol. 58(4):1023-1032 (2011).
Shpilfoygel et al., "Comparison of methods for instantaneous angiographic blood flow measurement", Medical Physics, vol. 26(6):862-871 (1999).
Sianos et al., "The SYNTAX score: an angiographic tool grading the complexity of coronary artery disease", Euro Intervention, vol. 1(2):219-227 (2005).
Siogkas et al., "Quantification of the effect of percutaneous coronary angioplasty on a stenosed right coronary artery", 2010 10th IEEE Intl. Conference on Information Technology and Applications in Biomedicine, Nov. 3-5, 210, pp. 1-4 (2010).
Slomka et al., "Fully automated wall motion and thickening scoring system for myocardial perfusion SPECT: Method development and validation in large population", Journal of Nuclear Cardiology, vol. 19(2):291-302 (2012).
Sprague et al., "Coronary x-ray angiographic reconstruction and image orientation", Medical Physics, vol. 33(3):707-718 (2006).
Sun et al., "Coronary CT angiography: current status and continuing challenges", The British Journal of Radiology, vol. 85:495-510 (2012).
Takarada et al., "An angiographic technique for coronary fractional flow reserve measurement: in vivo validation", International Journal of Cardiovascular Imaging, published online pp. 1-10, Aug. 31, 2012.
Termeer et al., "Visualization of myocardial perfusion derived from coronary anatomy", IEEE Transactions on Visualization and Computer Graphics, vol. 14(6):1595-1602 (2008).
Tomasello et al., "Quantitative coronary angiography in the interventional cardiology", Advances in the Diagnosis of Coronary Atherosclerosis, Chap. 14:255-272 (2011).
Tu et al., Assessment of obstruction length and optimal viewing angle from biplane X-ray angiograms, Int J Cardiovasc Imaging, vol. 26:5-17 (2010).
Tu et al., "In vivo assessment of optimal viewing angles from X-ray coronary angiography", EuroIntervention, vol. 7:112-120 (2011).
Tu et al., "In vivo assessment of bifurcation optimal viewing angles and bifurcation angles by three-dimentional (3D) quantitative coronary angiography", Int J Cardiovasc Imaging, published online Dec. 15, 2011, in 9 pages.
Tu et al., "The impact of acquisition angle differences on three-dimensional quantitative coronary angiography", Catheterization and Cardiovascular Interventions, vol. 78:214-222 (2011).
Tuinenburg et al., "Dedicated bifurcation analysis: basic principles", Int J Cardiovasc Imaging, vol. 27:167-174 (2001).
Voci et al., "Coronary flow: a new asset for the echo lab?", European Heart Journal, vol. 25:1867-1879 (2004).
Weickert et al., "A scheme for coherence-enhancing diffusion filtering with optimized rotation invariance", Computer Vision, Graphics, and Pattern Recognition Group, Technical Report, Computer Science Series, pp. 1-20 (2000).
Weickert, "Anisotropic diffusion in image processing", ECMI, published by Teubner Stuttgart, Germany, 181 pages (2008).
Weickert et al., "A scheme for coherence-enhancing diffusion filtering with optimized rotation invariance", Journal of Visual Communication and Image Representation, vol. 13(1-2):103-118 (2002).
Wong et al., "Quantification of fractional flow reserve based on angiographic image data", The International Journal of Cardiac Imaging, vol. 28(1):13-22 (2012).
Wong et al., "Determination of fractional flow reserve (FFR) based on scaling laws: a simulation study", Physics in Medicine and Biology, vol. 53:3995-4011 (2008).
Wong et al., "Automated technique for angiographic determination of coronary blood flow and lumen volume", Acad. Radiol. vol. 13:186-194 (2006).
Xu et al., "Snakes, shapes, and gradient vector flow", IEEE Transactions on Image Processing, vol. 7:359-369 (1998).
Yang et al., "Novel approach for 3-D reconstruction of coronary arteries from two uncalibrated angiographic images", IEEE Transactions on Image Processing, vol. 18(7):1563-1572 (2009).
Youssef et al., "Role of computed tomography coronary angiography in the detection of vulnerable plaque, where does it stand among others?", Angiology, vol. 1(2):1000111-1-1000111-8 (2013).
Zhang et al., "Quantification of coronary microvascular resistance using angiographic images for volumetric blood flow measurement: in vivo validation", Am J Physio Heart Circ vol. 300(6):H2096-H2104 (2011).
Invitation to Pay Additional Fees in Application No. PCT/IL2013/050869, mailed on Jan. 30, 2014, in 6 pages.
European Search Report in application No. EP 14708097.2, dated Aug. 3, 2017, in 7 pages.
European Search Report in application No. EP 14710059.8, dated Aug. 1, 2017, in 7 pages.
Invitation to Pay Additional Fees in Application No. PCT/IL2014/050923, mailed on Feb. 6, 2015, in 8 pages.
Invitation to Pay Additional Fees in Application No. PCT/IB2023/051186, mailed on May 25, 2023, in 33 pages.
Office Action with English translation in Chinese Application No. CN 201480014756.X, dated Mar. 7, 2017.
Office Action dated Dec. 24, 2015, in U.S. Appl. No. 14/866,098.
Official Action dated Dec. 23, 2016, from the U.S. Patent & Trademark Office re: U.S. Appl. No. 14/437,205, in 54 pages.
International Search Report and Written Opinion in application No. PCT/IL2014/050923, mailed on Jul. 10, 2015, in 17 pages.
International Preliminary Report on Patentability and Written Opinion in application No. PCT/IL2014/050923, mailed on May 6, 2016.
International Preliminary Report on Patentability and Written Opinion in application No. PCT/IL2013/050869, mailed on May 7, 2015.
International Search Report and Written Opinion in application No. PCT/IL2013/050869, dated May 23, 2014.
International Search Report and Written Opinion in application No. PCT/IL2014/050043, dated May 16, 2014.
International Preliminary Report on Patentability in application No. PCT/IL2014/050043, dated Jul. 30, 2015.
International Search Report and Written Opinion in application No. PCT/IL2014/050044, dated May 16, 2014.
International Preliminary Report on Patentability in application No. PCT/IL2014/050044, dated Jul. 30, 2015.
International Search Report and Written Opinion in application No. PCT/IL2014/050039, dated May 28, 2014.
International Preliminary Report on Patentability in application No. PCT/IL2014/050039, dated Jul. 30, 2015.
Office Action in European Application No. 1959185, dated Jul. 15, 2022.
European Communication in application No. 20162040.8, dated Sep. 2, 2020.
European Search Report in application No. 20165684.0, dated Aug. 12, 2020.

(56) References Cited

OTHER PUBLICATIONS

Applicant-initiated Interview Summary dated Oct. 4, 2016, in U.S. Appl. No. 14/040,688.
Office Action dated Aug. 15, 2016, in U.S. Appl. No. 14/040,688.
Applicant-initiated Interview Summary dated Dec. 23, 2016, in U.S. Appl. No. 14/761,079.
Office Action dated May 4, 2017, in U.S. Appl. No. 14/761,079.
European Office Action in application No. 13796169.4, dated Jul. 28, 2017.
Barrett et al., "Interactive live-wire 1-3 boundary extraction", Medical Image Analysis, Oxford University Press, vol. 1(4):331-341 (1997).
Chen et al., "3-D reconstruction of coronary arterial tree to optimize angiographic visualization", IEEE Transactions on Medical Imaging, vol. 19(4):318-336 (2000).
Marchenko, et al., "Vascular editor: from angiographic images to 3D vascular models", Journal of Digital Imaging, vol. 23:386-398 (2010).
Pijls et al., "Experimental basis of determining maximum coronary, myocardial, and collateral blood flow by pressure measurements for assessing functional stenosis severity before and after percutaneous transluminal coronary angioplasty", Circulation, vol. 87:1354-1367 (1993).
Wang et al., "Optimal viewing angle determination for multiple vessel segments in coronary angiographic image", IEEE Transactions on Nuclear Science, vol. 61(3):1290-1303 (2014).
Wang et al., "Global optimization angiographic viewing angles for coronary arteries with multiple segments", 35th Annual International Conference of the IEEE EMBS, pp. 2640-2643, Osaka, Japan, Jul. 3-7, 2013.
European Search Report in application No. 20162040.8, dated Dec. 14, 2023, in 6 pages.
Office Action with English translation in Japanese application No. 2022-124490, dated Feb. 27, 2024, in 18 pages.
Communication in European application No. 20190353.1, dated Apr. 3, 2024, in 5 pages.
Kern, "Serial lesion FFR made simple", Cath Lab Digest, vol. 20(9)(2012), in 2 pages, [retrieved on on Sep. 25, 2024], retrieved from the internet: https://www.hmpgloballearningnetwork.com/site/cathlab/articles/serial-lesion-ffr-made-simple.
Nijjer et al., "Pre-angioplasty instantaneous wave-free ratio pullback provides virtual intervention and predicts hemodynamic outcome for serial lesions and diffuse coronary artery disease", JACC: Cardiovascular Interventions, vol. 7(12):1386-1396 (2014).

\* cited by examiner

AUTOMATED MEASUREMENT SYSTEM AND METHOD FOR CORONARY ARTERY DISEASE SCORING

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD AND BACKGROUND OF THE INVENTION

The present invention, in some embodiments thereof, relates to the field of heart care, and more particularly, to tools for characterizing heart disease.

Many people with cardiovascular disease suffer from complex lesions, wherein a decision must be made whether to perform percutaneous coronary intervention (PCI), such as a stent, for example, or to perform coronary artery bypass surgery (CABG). Generally, if only one or two lesions are found, and these lesions are not in the main coronary vessels, PCI is recommended. However, in cases of multiple lesions (three or more), or when a lesion is found in the left main artery, the decision is based on many factors which are weighed subjectively by the interventional cardiologist and by the cardiac surgeon.

The SYNTAX Score is an angiographic tool used to characterize the coronary vasculature disease state and predict outcomes of coronary intervention based on anatomical complexity. SYNTAX Score grades the complexity of the coronary artery disease, which also allows for comparison between patients and for more effective communication between the doctors. This scoring calculation method has been recommended by professional societies of medical heart-care specialists as an integral part of the decision making process in complex cardiovascular cases.

SUMMARY OF THE INVENTION

According to an aspect of some embodiments of the present invention, there is provided a method of mammalian vascular state scoring, comprising: receiving vascular image data; determining automatically a plurality of subscore-related vascular metrics for each of a plurality of vascular segments, based on the received image data; determining subscores of a vascular state scoring tool based on the plurality of vascular metrics; and operating a score calculator for the vascular state scoring tool to calculate a score based on the subscores, the score being applicable to surgical intervention decision-making.

According to some embodiments of the invention, the determining of the subscore-related vascular metrics comprises determination of a vascular width metric function for the imaged state of the vascular segment, and determination of a corresponding width metric function for a modeled state of the vascular segment distinct from the imaged state.

According to some embodiments of the invention, the vascular metrics comprise a metric which is a function of vascular segment position.

According to some embodiments of the invention, the function of vascular segment position describes a vascular width metric.

According to some embodiments of the invention, the vascular image data is of the arterial vasculature of the heart.

According to some embodiments of the invention, the vascular state scoring tool is SYNTAX Score.

According to some embodiments of the invention, the subscores comprise all image data-based subscores comprised within the vascular state scoring tool.

According to some embodiments of the invention, the subscores comprise at least half of all image data-based subscores comprised within the vascular state scoring tool.

According to some embodiments of the invention, the determining of the vascular metrics comprises mapping measurement values to positions within the plurality of vascular segments.

According to some embodiments of the invention, the positions are examinable to determine position relative to branch points among the plurality of vascular segments.

According to some embodiments of the invention, the positions are associated with anatomically identifying vascular segment labels.

According to some embodiments of the invention, the vascular metrics comprise measurements of vascular segment stenosis.

According to some embodiments of the invention, at least one of the subscores is based on the measurements of vascular segment stenosis in association with vessel branch points.

According to some embodiments of the invention, the mapping represents relative locations of vascular segment stenosis lesions along vessel segments.

According to some embodiments of the invention, distances between the relative locations are associated with a local vascular segment width.

According to some embodiments of the invention, the mapping comprises representation of a vessel segment stenosis lesion in association with a plurality of post-lesion vessel widths.

According to some embodiments of the invention, the determining of vascular metrics comprises determining a vascular model representation for the at least one vascular segment based on the received imaged data.

According to some embodiments of the invention, the determining of vascular metrics comprises determining an unstenosed model representation for the at least one vascular segment based on the received image data.

According to some embodiments of the invention, the determining of vascular metrics comprises determining a severity of stenosis in the at least one vascular segment based on differences between the unstenosed model representation and the vascular model representation.

According to some embodiments of the invention, the determining comprises binary segmentation of a vascular lesion contour region.

According to some embodiments of the invention, the vascular state scoring tool is a modification of the SYNTAX Score scoring tool.

According to some embodiments of the invention, the vascular image data is 3-dimensional.

According to some embodiments of the invention, the vascular image data is 2-dimensional.

According to some embodiments of the invention, the operating comprises automatic parameter entry to the scoring tool.

According to some embodiments of the invention, the determining automatically comprises determining a parameter describing an uncertainty of the at least one morphology metric.

According to some embodiments of the invention, the vascular metrics include a measure of vascular occlusion.

According to some embodiments of the invention, the vascular metrics include a measure of lesion length.

According to some embodiments of the invention, the vascular metrics include a measure of vascular tortuosity.

According to some embodiments of the invention, the vascular metrics include a measure of relative lesion positioning.

According to some embodiments of the invention, the vascular metrics include a count of vascular branches.

According to some embodiments of the invention, the vascular metrics include recognition of an area of a thrombus.

According to some embodiments of the invention, the vascular metrics include recognition of a calcification.

According to some embodiments of the invention, the vascular metrics include a measure of vascular branch diameter beyond a lesion point.

According to some embodiments of the invention, the method comprises receiving an output from said vascular state scoring tool; and determining to perform percutaneous angioplasty in an imaged patient based on said received output; wherein at the time of said determination, the patient remains catheterized from the imaging procedure producing said received vascular image data.

According to an aspect of some embodiments of the present invention, there is provided a system for automatic determination of parameters for a mammalian vascular state scoring tool, comprising: a subscore extractor functionally connectable to at least one vascular image data source-configured to determine at least one vascular disease-related metric based on vascular image data received from the image data source, and determine at least one parameter based on the at least one metric; and a vascular state score calculator-configured to receive a plurality of parameters comprised in vascular state subscores, at least from the subscore extractor, and compose the subscores into a vascular state score; the vascular state score being applicable to surgical intervention decision-making.

According to some embodiments of the invention, the subscore extractor comprises a metrics extractor, operable to receive the vascular image data and extract from it the at least one vascular disease-related metric.

According to some embodiments of the invention, the metrics extractor comprises a vascular tree reconstructor, operable to reconstruct a data structure representing a connected group of vascular segments from the vascular image data.

According to some embodiments of the invention, the data structure represents three-dimensional spatial relationships among the connected group of vascular segments.

According to some embodiments of the invention, the data structure represents two-dimensional spatial relationships among the connected group of vascular segments.

According to some embodiments of the invention, the data structure represents branch connection relationships among the connected group of vascular segments.

According to some embodiments of the invention, the metrics extractor comprises a stenosis determiner, operable to determine a degree of stenosis within vessels imaged by the vascular image data, based on a data structure representing at least one vascular segment from the vascular image data.

According to some embodiments of the invention, the metrics extractor comprises a metrics module, operable to determine for a vascular segment one or more morphometric functions along the length of the segment.

According to some embodiments of the invention, the one or more morphometric functions produce results selected from among the group of vessel diameter, vessel radius, vessel cross-section, vessel curvature, and vessel wall curvature.

According to some embodiments of the invention, the system is functionally connectable to a parameter data source for receiving at least one of the plurality of parameters.

According to some embodiments of the invention, the parameter data source comprises a user interface suitable for entering at least one of the plurality of parameters.

According to some embodiments of the invention, the subscore extractor comprises a parameter compositor, operable to determine at least one parameter based on the at least one metric.

According to some embodiments of the invention, the vascular state score calculator comprises a parameter finalizer, operable for at least one of correcting and reviewing the plurality of parameters prior to an operation to compose the subscore into a vascular state score.

According to some embodiments of the invention, the operability for at least one of correcting and reviewing comprises displaying annotations of the vascular image data based on data produced during the determination of the at least one vascular disease-related metric.

According to an aspect of some embodiments of the present invention, there is provided a method of determining an unstenosed model of a mammalian vascular tree, comprising: receiving image data of the vascular tree; reconstructing a vascular model representation for at least one vascular segment based on the received imaged data; determining an unstenosed model representation for the at least one vascular segment based on the reconstructed vascular model representation; and determining a severity of stenosis in the at least one vascular segment based on differences between the unstenosed model representation and the vascular model representation.

According to some embodiments of the invention, the determining of an unstenosed model representation comprises selecting a model representation by minimizing deviation of the unstenosed model morphometry from the vascular model morphometry according to a weighting function.

According to some embodiments of the invention, the weighting function weights unstenosed model vessel diameter deviations below the vessel diameter of the vascular model more heavily than unstenosed model diameter deviations thereabove.

According to some embodiments of the invention, the weighting function is iteratively recalculated after determining a first or subsequent unstenosed model representation, and the unstenosed model representation recalculated accordingly, until a criterion of stability for the unstenosed model representation is satisfied.

According to some embodiments of the invention, the weighting function weights locations in end portions of the vascular segment more heavily than points away from the end portions.

According to an aspect of some embodiments of the present invention, there is provided a method of determining an unstenosed model of a region of bifurcation in a mammalian vascular tree, comprising: receiving image data of the region of bifurcation; determining a vascular model representation of the region of bifurcation; generating an interpolated vascular representation passing between two branches of the bifurcation based on the vascular model representation; comparing the interpolated vascular representation with the vascular model representation to obtain an estimate of stenosis through the region of bifurcation.

According to some embodiments of the invention, the determining of a vascular model representation comprises selecting of at least one image plane intersecting the bifurcation.

According to some embodiments of the invention, the selecting comprises mapping three-dimensional coordinates obtained from the received image data to determine the image plane.

According to some embodiments of the invention, the vascular model representation comprises determination from a plurality of the image planes.

According to some embodiments of the invention, the interpolation is between at least one constraint point selected from each of the branches.

According to some embodiments of the invention, the interpolation is between at least two constraint points selected from each of the branches.

According to some embodiments of the invention, the interpolation comprises interpolation of at least two vascular wall profiles between the constraint points.

According to an aspect of some embodiments of the present invention, there is provided a method of determining an unstenosed model of a mammalian vascular tree, comprising: receiving an initial vascular segment model of a mammalian vascular tree; the initial model comprising functions of a vascular width metric for the segments described therein; composing a long segment function by an ordering of the vascular width metric functions; updating the long segment function according to a weighting function, the weighting function comprising at least one constraint for the vascular width metric; and updating the initial vascular segment model based on the updated long segment function.

According to some embodiments of the invention, the updating of the long segment function occurs iteratively.

According to some embodiments of the invention, the at least one constraint comprises a constraint for a monotonic decrease in the vascular width metric from a trunk portion of the long segment.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. In the drawings.

DESCRIPTION OF SPECIFIC EMBODIMENTS OF THE INVENTION

Figure 1:
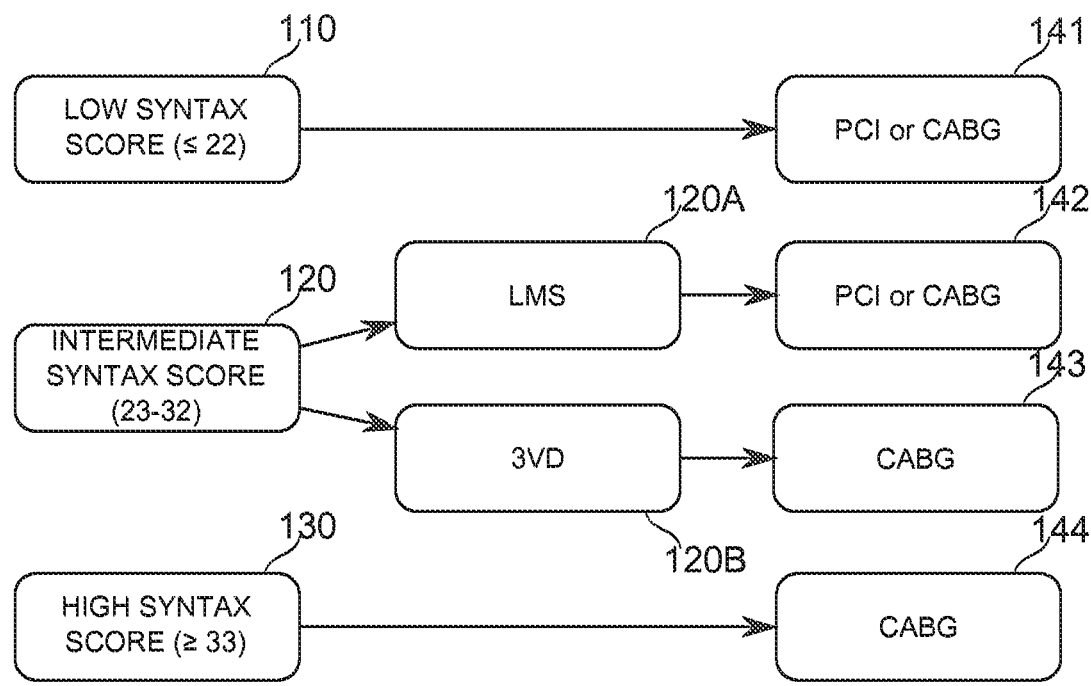
FIG. 1 is a block diagram illustrating a decision tree based on the SYNTAX Score outcome and the type of complex lesion, according to some exemplary embodiments of the invention.

The present invention, in some embodiments thereof, relates to the field of heart care, and more particularly, to tools for characterizing heart disease.

Overview

An aspect of some embodiments of the invention relates to automated determination of parameters based on vascular images, used to calculate a vascular disease score. In some embodiments, the imaged blood vessels are cardiac blood vessels.

In some embodiments of the invention, a cardiac disease score is calculated according to the SYNTAX Score calculation method. In some embodiments, a cardiac disease score is calculated by a SYNTAX Score alternative, derivative and/or successor vascular state scoring tool (VSST). Alternative VSST approaches potentially include, for example, a "Functional SYNTAX Score" (integrating physiological measurements—for example, vascular flow capacity, vascular elasticity, vascular autoregulatory capacity, and/or another measure of vascular function—with a SYNTAX Score-like tool), or a "Clinical SYNTAX Score" (integrating clinical variables-for example, patient history, and/or systemic and/or organ-specific test results—with a SYNTAX Score-like tool). Examples also include the AHA classification of the coronary tree segments modified for the ARTS study, the Leaman score, the ACC/AHA lesions classification system, the total occlusion classification system, and/or the Duke and ICPS classification systems for bifurcation lesions.

In some embodiments of the invention, metrics describing a vascular state are determined based on vascular imaging data. In some embodiments, the metrics are expressed, for example, as functions of vascular position (for instance, one-dimensional functions of position along a vascular segment length). The metrics express, in some embodiments, morphometric quantities such as vascular width (optionally as a diameter, radius, or cross-sectional area), vascular curvature, or another morphometric quantity. In some embodiments, the metric is of another morphological or functional measurement, such as a determined flow capacity, vascular elasticity, and/or vascular wall composition. In some embodiments, vascular state metrics determined from images comprise identifying information relative to a standard vascular atlas or other system of nomenclature.

In some embodiments, vascular state metrics are converted automatically into sub-scores for a VSST by a further operation, tailored, for example, to the specific requirements of a VSST such as SYNTAX Score. In some embodiments, sub-scores are determined based on vascular state metrics composed with operator- or network-provided information related to a subject and/or to vascular imaging data.

Potentially, automatic determination of VSST parameters reduces subjectivity and/or training variability affecting a VSST outcome. Potentially, automatic determination reduces the time and/or training required to determine a VSST score. Reducing the time and/or training required to effective determine a SYNTAX Score, for example, potentially increases compliance with vascular disease evaluation guidelines recommending using SYNTAX Score as a basis for medical decision making in cardiology. A potential advantage of reducing SYNTAX Score and/or other VSST outcome variability is increased reliability of score calculation, and/or of raw data available for future versions of SYNTAX Score and/or another VSST. A potential benefit of rapid automated or semi-automated SYNTAX Score determination, for example, is to allow a more rapid determination based on the score of a vascular intervention treatment. Potentially, the determination speed-up is sufficient to allow a single catheterization procedure to be performed comprising both diagnostic imaging and treatment intervention.

In some embodiments of the invention, the VSST score is generated entirely automatically based on provided image data and optionally other information. In some embodiments, VSST scoring is guided by an operator, for example, by selection of relevant image and/or segment regions for VSST scoring analysis. In some embodiments, operator guidance comprises segment identification, for example by providing a segment-identifying label and/or by identifying key points on a segment permitting machine identification thereof.

An aspect of some embodiments of the invention relates to the production and/or use of an astenotic model of a mammalian vasculature, or "virtual revascularization", usable, for example, in vascular disease state scoring.

In some embodiments of the invention, an astenotic vasculature model comprises a computer-generated and/or computer-stored data structure, for which relatively undiseased portions of an imaged vasculature have provided a framework for interpolating and/or extrapolating across diseased vascular regions to describe metrics relating to a relatively undiseased state therein. In some embodiments of the invention, the difference between an imaged state and a determined relatively undiseased state comprises one or more metrics of disease state. In some embodiments, the astenotic model comprises blood vessel segments extending between vascular branch points. In some embodiments, the astenotic model comprises regions of branching, for example, bifurcations and/or trifurcations.

Some embodiments of the invention described herein are contemplated for use with the SYNTAX scoring method, described, for example, at www(DOT)syntaxscore(DOT)com. However, the invention is also contemplated for use with successor and/or alternative scoring methods, including future versions of SYNTAX and/or alternative scoring methods which make use of parameters determinable as described hereinbelow. It should furthermore be understood that herein, wherever SYNTAX, SYNTAX Score, SYNTAX Score calculation, and similar terminology is used, there is implicit reference made to all such successor and/or alternative scoring methods, with changes as necessary as would be clear to one skilled in the art working on the basis of descriptions herein.

Embodiments of the invention described herein are described with particular reference to cardiac vasculature. In some embodiments—additionally or alternatively—the vasculature is of another organ, for example, a kidney, a retina, and/or a brain. It should be understood, where cardiac vasculature is described in particular, that implicit reference is also made to embodiments relating to the vasculature of another organ, with changes as necessary as would be clear to one skilled in the art working on the basis of descriptions herein.

To emphasize the breadth of scoring methods and vascular targets contemplated for some embodiments of the invention, the term VSST (Vascular State Scoring Tool) is also used herein, without detracting from the general meaning attributed to the phrase "SYNTAX Score" and its derivatives.

Definitions and Abbreviations

SYNTAX Trial
Well-known prospective multi-site clinical trial to assess PCI vs. CABG efficacy. Described, for example, by Kappetein (2006).
SYNTAX Score
Diagnostic tool, developed in association with the SYNTAX trial, for scoring complexity of coronary artery disease as an aid for planning treatment.

SYNTAX Score Outcome

A value calculated using the SYNTAX Score calculation procedure. Also called a "SYNTAX score" (no capitalization of "score") herein.

VSST

Vascular State Scoring Tool. Term used herein for general reference to scoring tools, and in particular image-based scoring tools, used for determining a vascular state. The SYNTAX Score is an example of a VSST, but versions and variants of and/or alternatives to SYNTAX relying on parameters calculated as described herein should also be understood to be encompassed by this term.

VSST Outcome

A value reflecting vascular disease state calculated using a vascular state scoring tool. Also referred to as a VSST score.

PCI

Percutaneous Coronary Intervention. Sometimes known as coronary angioplasty or angioplasty. A non-surgical procedure used to treat the stenotic coronary arteries of the heart found in coronary heart disease. PCI treatments include balloon-opening and stent implantation.

CABG

Coronary Artery Bypass Graft. Sometimes known as heart bypass or bypass surgery. Surgical procedure in which blood vessels are grafted onto heart arteries to bypass stenotic coronary arteries of the heart found in coronary heart disease.

LMS

Left Main Stem. Arterial segment between the ostium of the left coronary artery through bifurcation into left anterior descending and left circumflex branches.

3VD

Three-vessel disease. Vascular lesion in three or more vessels.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways. In other instances, well-known methods, procedures, components and structures may not have been described in detail so as not to obscure the present invention.

Exemplary VSST (SYNTAX Score)

Reference is now made to FIG. 1, which is a block diagram illustrating a decision tree based on the SYNTAX Score outcome and the type of complex lesion; according to some exemplary embodiments of the invention.

At block 110, a low SYNTAX score (22) comprises an indicator for either PCI or CABG treatment (block 141). At block 130, a high SYNTAX score (33) is an indicator for preferring CABG revascularization treatment (block 144).

An intermediate SYNTAX score (23-32, block 120) comprises an indicator for either PCI or CABG (block 142) when the lesion is in the left main stem (LMS, block 120A), and is generally an indicator for CABG (block 143) when the lesion is in three or more vessels, otherwise known as 3-vessel disease (3VD, block 120B).

In calculating a SYNTAX score, a physician answers a series of questions relating to the location and size of lesions; including, for example: degree of occlusion (for example, a threshold occlusion of >50% is provided for in the scoring instructions), shape and length, presence of thrombus, and/or tortuosity of the blood vessel. Herein, the answer to each such question is referred to as a "parameter" of a scoring tool. Additionally or alternatively, the answer to the question is referred to as a "subscore" of a weighted score produced by such a scoring tool Coronary vascular images are the basis on which many of the questions are answered. Optionally, a PCI treatment is undertaken immediately or on the same day upon a decision to use this treatment. Typically, the more invasive and potentially more complicated CABG treatment is scheduled for a different patient visit. It is a potential advantage to make a scoring decision quickly, in order to release a patient and/or begin a treatment option with reduced delay. In some embodiments, the calculation of a SYNTAX Score is performed, for example, within a minute of imaging, within 2-4 minutes, within 5-10 minutes, within 5-15 minutes, or within another period of time suitable for allowing a patient to remain on a procedure table while a clinical intervention decision is determined.

A SYNTAX Score calculator is available for entering answers manually on a website (www(DOT)syntaxscore (DOT)com). In some cases, evaluation is performed immediately after imaging of a patient. Answering generally takes several minutes (20-30 minutes is typical), with speed and accuracy of answers based on the skill and/or experience of the evaluating practitioner.

In some embodiments of the invention, one or more parameters of a VSST are determined automatically, using techniques of image processing and/or analysis. In some embodiments, the automatic determination is based on two-dimensional or three-dimensional images from sources including, for example, angiographic images, CT, MRI, IVUS, and/or OCT.

In some embodiments, two-dimensional images from an angiographic procedure are converted into a three-dimensional image, and lesions within the vessel are identified and entered as VSST parameters to arrive at a quick, objective SYNTAX score during the procedure. In some embodiments, VSST parameters are determined directly from two-dimensional images.

In some embodiments of the present invention, automatically determined values are provided as parameters to a VSST such as SYNTAX Score in real-time during a catheterization procedure, or following imaging.

Potentially, a reduced time of SYNTAX Score calculation provides an advantage by allowing a patient to be kept catheterized for a possible PCI treatment while waiting for a shorter period, and/or by reducing the need for recatheterization of a patient who has been temporarily released from a procedure room pending a treatment decision. Potentially, a reduced time and/or effort of scoring leads to increased use of a VSST such as SYNTAX Score as a tool for clinical decision-making.

In some embodiments of the invention, parameters of another VSST based on geometric, clinical, or functional factors are determined.

VSST Parameter Algorithm

Figure 2:
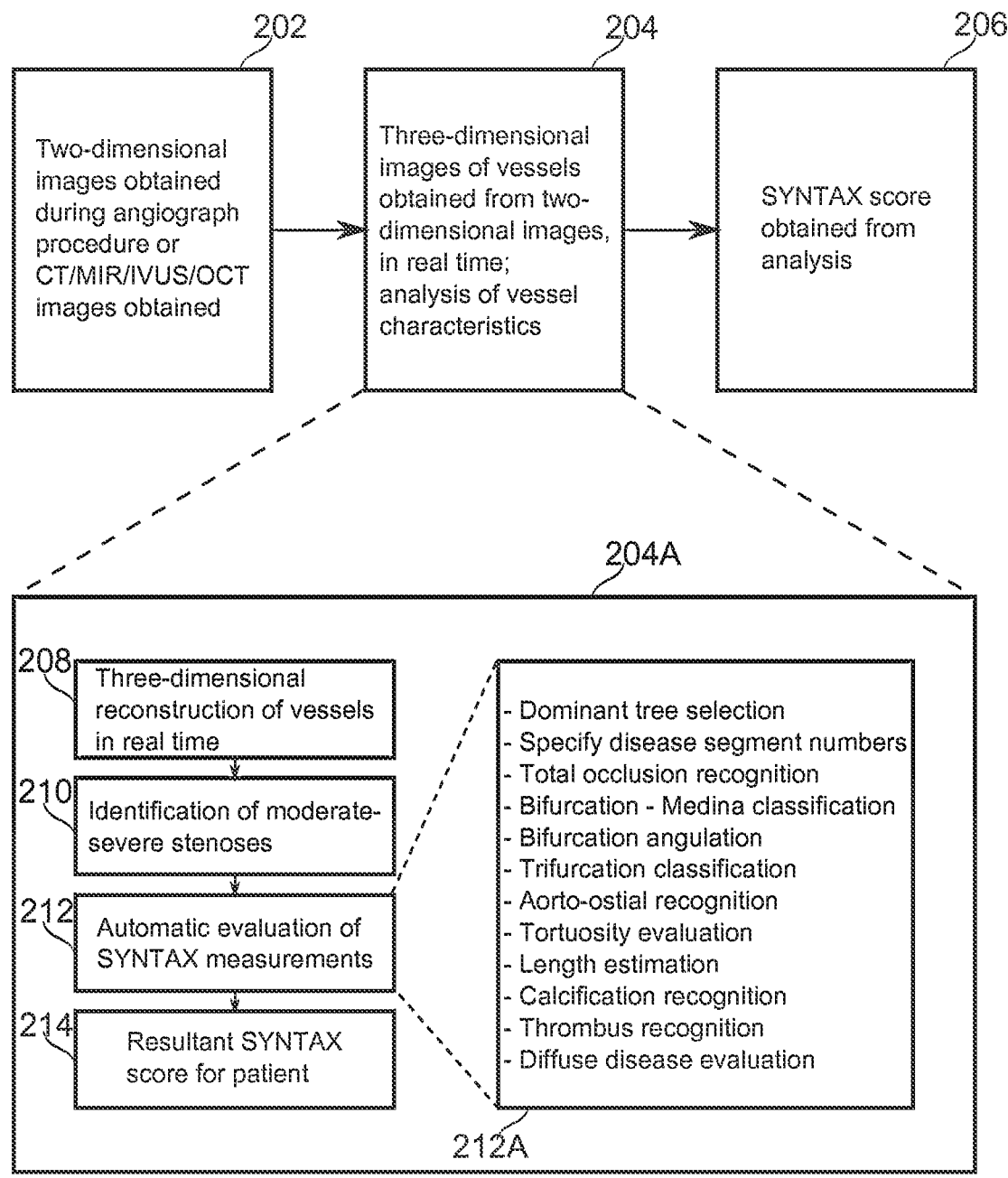
FIG. 2 is a block-diagram illustration of operations of an algorithm for automated SYNTAX Score determination, according to some exemplary embodiments of the invention.

Reference is now made to FIG. 2, which is a block-diagram illustration of operations of an algorithm, according to some exemplary embodiments of the stages.

At block 202, in some embodiments, two-dimensional images comprising the coronary arteries are obtained. In some embodiments, the two-dimensional images comprise X-ray angiograms, sections of CT 3-D imagery of the coronary arteries, or imagery obtained by, for example, MRI, IVUS, or OCT.

At block 204, in some embodiments, image processing and analysis and VSST score calculation is performed. Block 204A describes these operations in more detail.

At block 208, in some embodiments, a three-dimensional reconstruction of the vessels of an individual patient is performed, based on two-dimensional projections of the coronary arteries during a diagnostic catheterization. In some embodiments, this occurs in real-time, while the patient is undergoing catheterization together with imaging. In some embodiments, two-dimensional images are used directly in further image processing.

Figure 3:
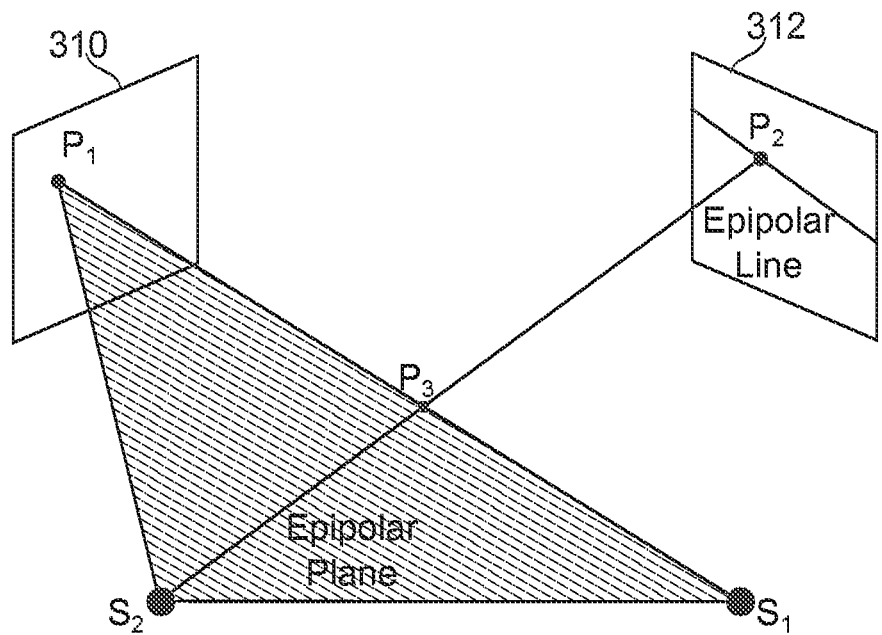
FIG. 3 is a schematic illustration showing principles of three-dimensional reconstruction by use of epipolar geometry, according to some exemplary embodiments of the invention.

Reference is now made to FIG. 3, which is a schematic illustration showing principles of three-dimensional reconstruction by use of epipolar geometry, according to some exemplary embodiments of the invention. FIG. 3 shows two exemplary image planes 310, 312 whereupon images of a target object point P3 are projected to P1 and P2, respectively, from radiant sources S1, S2. The relative positions of P1, P2, S1, and S2 are known, while the position of P3 in space is to be determined from these known positions. P3 is between S1 and P1, so it lies somewhere along the path between them. This path in turn has a projection onto the image plane of P2, (marked Epipolar Line), determinable from the intersection of the Epipolar Plane defined by S1, S2, and P1 with the image plane P2. The position of P2 along the Epipolar Line provides the remaining information needed to locate P3 in space. This concept is applicable to multiple image planes. Approaches which comprise three-dimensional reconstruction of vascular information from two-dimensional source data have been described (Pellot, 1994; Sprague, 2006; Andriotis, 2008). Reference is also made to U.S. Patent Application 61/752,526 by the Applicant, which is incorporated herein in its entirety by reference.

In some embodiments, based on reconstruction performed, for example, as m FIG. 3, a stereo reconstruction of the coronary tree is performed, using a series of spatially separated two-dimensional projections. Reconstruction produces a unified 3-D coronary tree. In some embodiments, for each vessel the location (x,y,z) and radius (R) is defined in the reconstruction. In some embodiments, the hierarchy between vessels, for example, the connections between vessel segments and/or their position relative to vessel branching points is definable with reference to a 3-D reconstruction.

Figure 5:
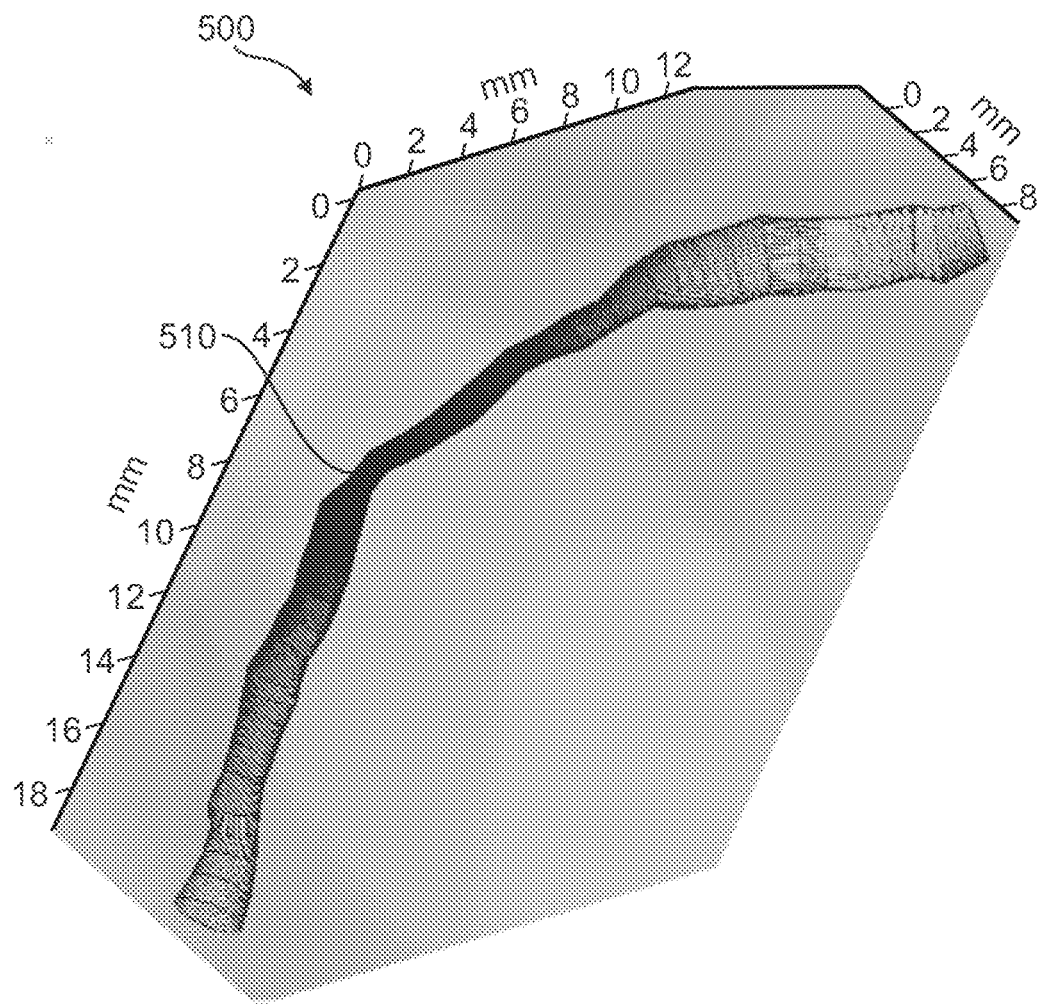
FIG. 5 illustrates a three-dimensionally reconstructed stenotic area along a vessel segment, according to some exemplary embodiments of the invention.

Reference is now made to FIG. 5, which illustrates a three-dimensionally reconstructed stenotic area 510 along a vessel segment 500, according to some exemplary embodiments of the invention. The gray scale indicates the radius along the vessel centerline (darker is narrower). Such a segment can be extracted, for example, from angiographic CT, MRI, PET, OCT, and/or IVUS. Methods of coronary angiography imaging are reviewed, for example, in Youssef (2013).

MDCT (multi-detector computed tomography) or CT (computed tomography) measures tissue and/or contrast agent attenuation of source X-ray radiation. Typical resolution is 200-500 μm, depending on specifics of the implementation.

MRI (magnetic resonance imaging) uses nuclear magnetic resonance properties of an endogenous or exogenously introduced contrast basis. Typical resolution may be 1 mm, down to 350 μm, depending on implementation.

PET (positron emission tomography) uses detection of emitted radiation from tracers. Typical resolution is 4-5 mm OCT (optical coherence tomography) measures backscattered light as a function of time (and/or, in some implementations, frequency). Typical resolution is 4-20 μm.

IVUS (intravascular ultrasound) operates by converting the intensity of backscattered sound signals (which varies by target encountered) into image representations. Typical resolution is about 150 μm.

In some embodiments of the invention, a two-dimensional vascular tree is recreated from one or more appropriate two-dimensional images or image sections. In some embodiments, manual guidance is accepted for determining which two-dimensional images comprise useful targets for image analysis of one or more vascular segments. A potential advantage of proceeding from a two-dimensional image is a reduced complexity of imaging procedure and/or a reduced computation time for vascular reconstruction from the image data.

A potential advantage of developing a vascular tree from a three-dimensional reconstruction is representation of depth information. This allows improved accuracy, for example, of measures of length and/or tortuosity, which are potentially reduced in 2-D due to foreshortening artifacts. Also for example, 3-D reconstruction potentially resolves ambiguities due to structures which cross over one another in 2-D images. Three-dimensional reconstruction also allows structural analysis from multiple angles, which potentially allows obtaining more accurate metrics for vascular features such as occlusion percentage and/or thrombus.

In some embodiments of the invention, the output of block 208 comprises a reconstruction of the complete coronary artery tree, including the right coronary artery and the left coronary arteries. In some embodiments the first stage results in a partial sub-tree reconstruction-the right coronary artery, the left coronary arteries, and/or any sub-branch of them. In some embodiments, a number/name of at least one segment is provided, for example to allow orientation of the reconstructed tree relative to the segment labeling used by the VSST.

In some embodiments of the invention, a hierarchical tree, complete or partial, of arterial centerlines is derived from the reconstructed artery tree. In some embodiments, at points along these centerlines, vessel radius, curvature and tortuosity are determined At block 210, in some embodiments, the tree structure serves as for extracting the significant stenosis areas, based on the analysis of the vessels' radii. SYNTAX Score, for example, defines significant stenosis as to moderate to severe stenosis having >50% lumen blockage.

At block 212, in some embodiments, specific parameters corresponding to each significant stenosis located on the previous stage are determined, according to the SYNTAX Score or other VSST specifications. In some embodiments, determined parameters include one or more of the following parameters (listed at block 212A):

Sub-tree dominance.
Anatomical identification (for example, branch position) of the diseased segment. In some embodiments, lesions in some segments are weighted more heavily than in others.
Recognition of total occlusion. In some embodiments, total occlusions are further classified, for example, according to known age, presentation of a blunt stump, proximity to side branches, and/or bridging by shunting vessels.
Bifurcation-Medina classification.
Bifurcation angulation.
Trifurcation classification.
Recognition of aorto-ostial proximity.
Tortuosity evaluation.
Length estimation.

Calcification recognition.

Thrombus recognition.

Diffuse disease evaluation.

In some embodiments, most (for example, at least seven) or all of the foregoing parameters are determined Parameter calculations made based on automatic image processing and analysis operations provide a potential advantage in being not subject to subjective assessments by a practitioner.

At block 214, the results are compiled into a SYNTAX Score (or other VSST) outcome, and at block 206, the outcome is made available from the analysis.

System for Vascular State Scoring

Figure 7:
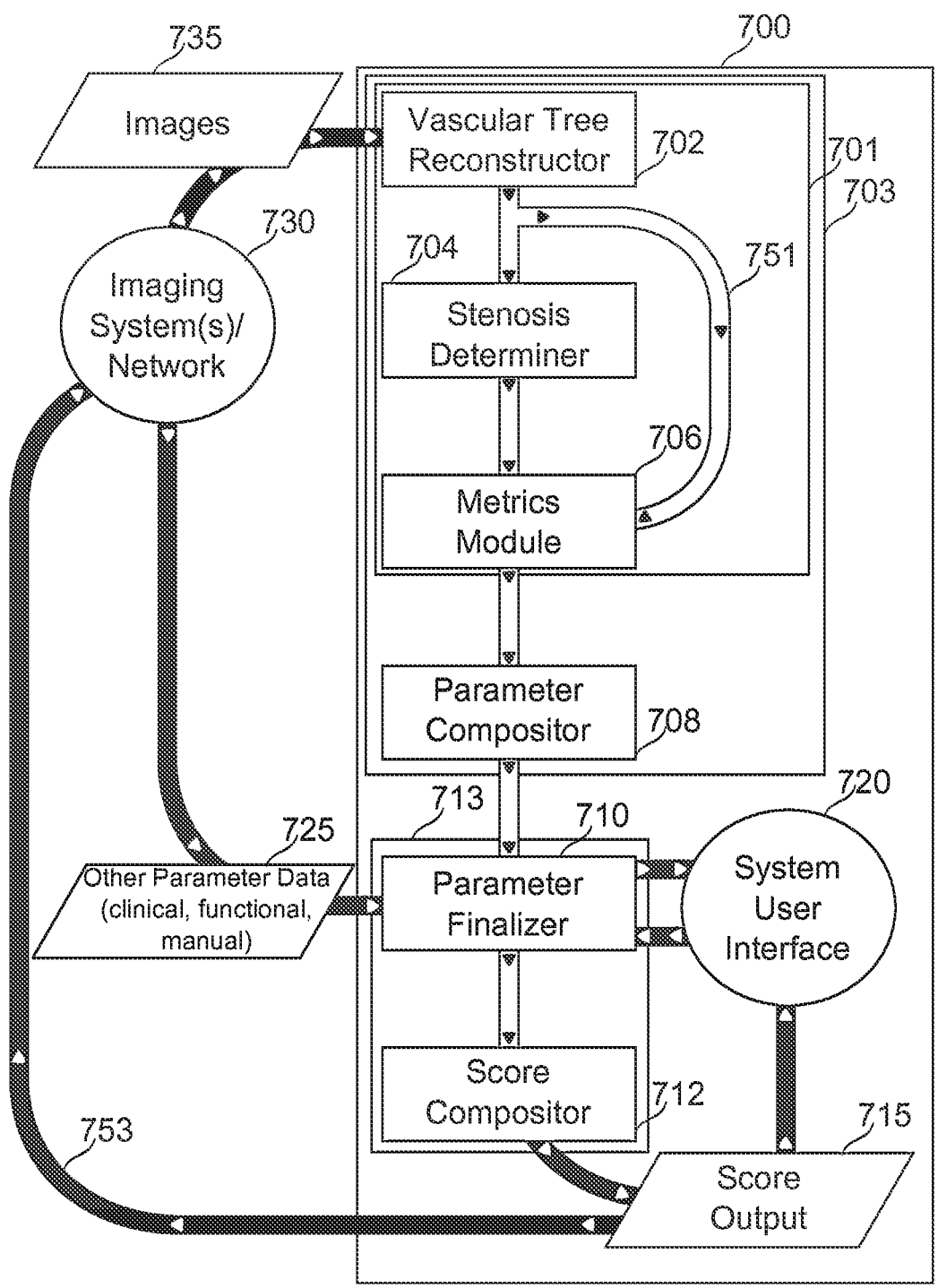
FIG. 7 is a simplified schematic of an automatic vascular state scoring tool scoring system, according to some exemplary embodiments of the invention.

Reference is now made to FIG. 7, which is a simplified schematic of an automatic VSST scoring system 700, according to some exemplary embodiments of the invention.

In FIG. 7, broad white pathways (for example, pathway 751) denote simplified paths of data processing through the system. Broad black pathways (for example, pathway 753) denote external data connections or connections to the system user interface 720. Black pathway data content is labeled by overlying trapezoidal blocks.

The vascular tree reconstructor 702, in some embodiments of the invention, receives image data 735 from one or more imaging systems or a system-connected network 730. Stenosis determiner 704, in some embodiments, determines the presence of stenotic vascular lesions based on the reconstructed vascular tree. In some embodiments, metrics module 706 determines additional metrics related to the disease state of the vascular tree, based on the reconstructed vascular tree and/or determined stenosis locations and other measurements.

In some embodiments, metrics extractor 701 comprises functions of vascular tree reconstructor 702, stenosis determiner 704, and/or metrics module 706. In some embodiments, metrics extractor 701 is operable to receive image data 735, and extract from it a plurality of vascular state metrics, suitable, for example, as input to parameter compositor 708.

In some embodiments, parameter compositor 708 converts determined metrics into subscore values (for example true/false values) which comprise parameters that "answer" vascular state scoring questions, and/or are otherwise are mapped to particular operations of a VSST scoring procedure.

In some embodiments, subscore extractor 703 comprises functions of vascular tree reconstructor 702, stenosis determiner 704, metrics module 706, and/or parameter compositor 708. In some embodiments, subscore extractor 703 comprises functions of metrics extractor 701. In some embodiments, subscore extractor 703 is operable to receive image data 735, and extract from it one or more VSST subscores, suitable as input for score calculator 713.

Parameter finalizer 710, in some embodiments, ensures that parameter data provided is sufficiently complete and correct to proceed to final scoring. In some embodiments, corrections to automatically determined parameters are determined at finalizer 710, optionally under operator supervision through system user interface 720. In some embodiments, lacunae in automatically provided parameter data are filled: for example, by user input from system user interface 720; or by other parameter data 725 provided, for example, from another diagnostic system or a network providing access to clinical data.

Score compositor 712, in some embodiments, composes the finalized outputs into a weighted score output 715 based on the determined parameters for the score. The score is made available, for example, over the system user interface or to networked resources 730.

In some embodiments of the invention, score calculator 713 comprises functions of the parameter finalizer 710 and/or score compositor 712. In some embodiments, score calculator 713 is operable to receive composited parameters and/or subscores (for example from parameter compositor 708 and/or subscore extractor 703), and convert them to a VSST score output 715.

In some embodiments of the invention, intermediate results of processing (for example, the reconstructed vascular tree, various metrics determined from it, and or parameter determinations) are stored in permanent or temporary storage on storage devices (not show) of the system 700, and/or on a network 730.

The scoring system 700 has been described in the context of modules which, in some embodiments of the invention, are implemented as programmed capabilities of a digital computer. It should be understood that the underlying system architecture may be implemented in various ways comprising embodiments of the invention; for example, as a single or multiple-process application and/or as client-server processes running on the same or on different computer hardware systems. In some embodiments of the invention, the system is implemented in code for execution by a general purpose processor. In some embodiments, part or all of the functionality of one or more modules is provided by an FPGA or another dedicated hardware component such as an ASIC.

To provide one example of a client-server configuration, a subscore extractor 703 is implemented as a server process (or group of server-implemented processes) on one or more machines remote to a client computer which implements modules such as the score calculator 713 and user interface 720. It should be understood that other divisions of modules described herein (or even divisions within modules) are encompassed by some embodiments of the invention. A potential advantage of such a division may be, for example, to allow high-speed dedicated hardware to perform computationally intensive portions of the scoring, while providing an economy of scale by allowing the hardware to be shared by multiple end-users. Such a distributed architecture potentially also provides advantages for maintenance and/or distribution of new software versions.

Stenosis Determination

Figure 4A:
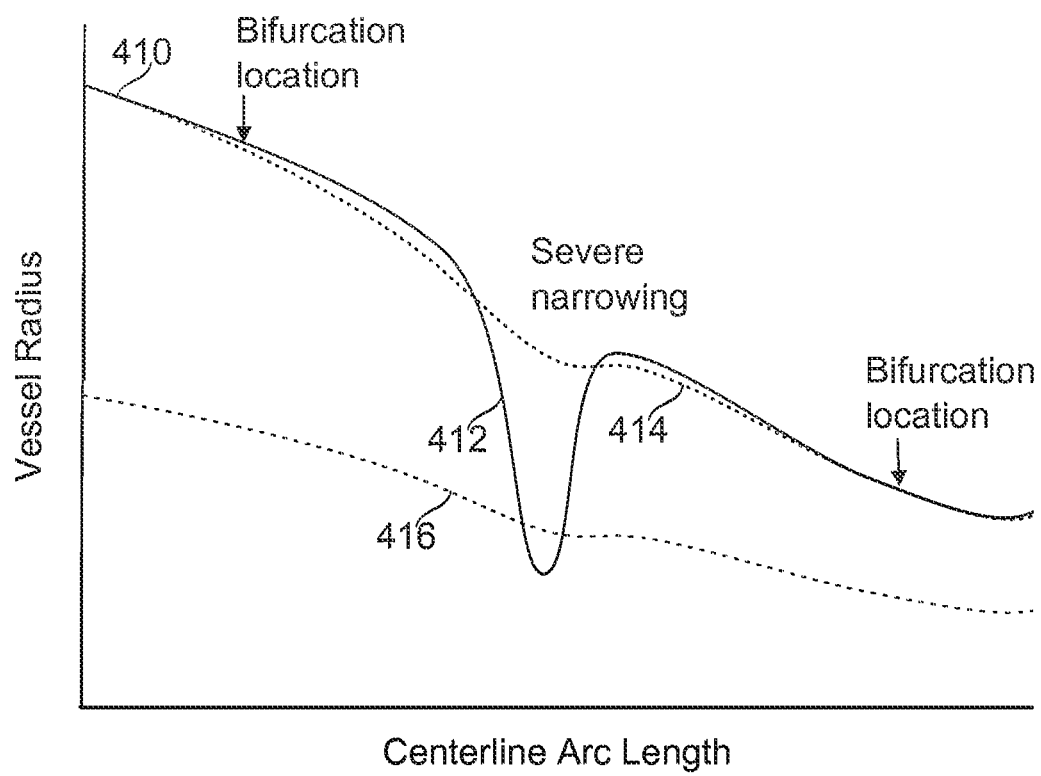
FIGS. 4A-4B schematically illustrate an example of a stenotic determination, according to some exemplary embodiments of the invention.
Figure 4B:
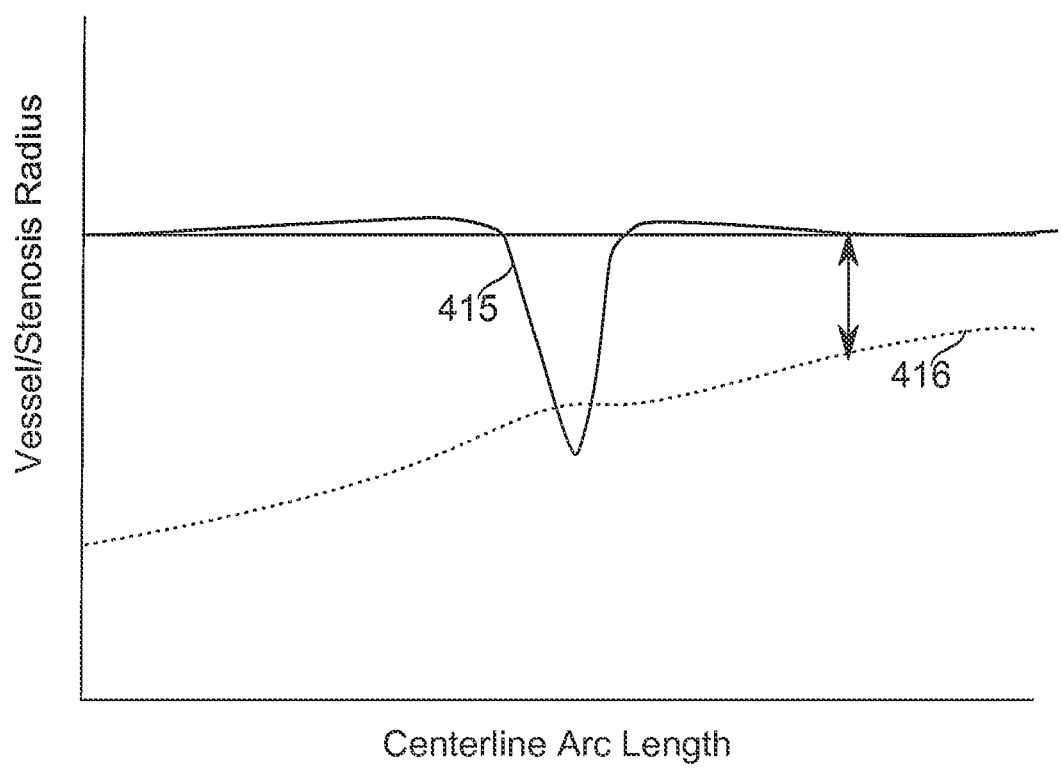

Reference is now made to FIGS. 4A-4B, which schematically illustrate an example of a stenotic determination, corresponding to the method a block 210, according to some exemplary embodiments of the invention.

The plot 410 in FIG. 4A shows radius (Vessel Radius) along a vessel segment (Centerline Arc Length). In some embodiments of the invention, measurements required for the SYNTAX Score or other VSST score can be extracted from such a one-dimensional function $r=f(s)$, where r is the vessel radius, and s is the arc-length.

In some embodiments of the invention, for example, a severe stenosis 412 is automatically identified by means of a high-pass filter. Plot 415 is the high-pass filter result. Subtracting the plot 415 from plot 410 obtains plot 414, which approximates the un-stenosed vessel width. Plot 416 represents the half-width of plot 415, representing, for some embodiments, the threshold between a scored and an unscored stenosis. Inverted and superimposed on plot 415, a sufficiently severe stenosis reveals itself where the plot 415 crosses inverted plot 416. Additionally or alternatively, a very positive and/or negative slope along a portion of plot 415 indicates a region of abrupt change.

In some embodiments of the invention, a lesion length is determined, for example by a metric such as width at a percentage occlusion relative to the maximum occlusion. In some embodiments, this percentage is 5%, 10%, 20%, or another percentage. In some embodiments, a lesion length is determined by a slope inward from the vascular wall above a threshold, for example, a change of 1 part in 3 (occlusion depth-to-length), 1 part in 5, 1 part in 10, or another slope. In some embodiments, a second or higher slope derivative is the basis of a total lesion length determination.

Stenosis Determination-Alternative Embodiments

Figure 8:
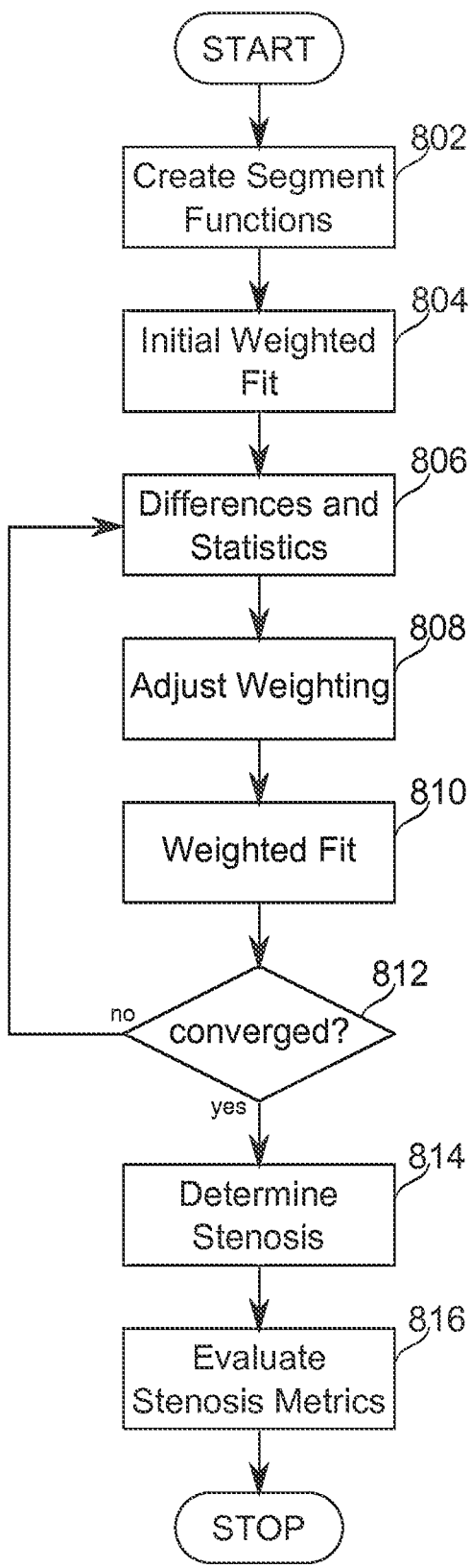
FIG. 8 is a simplified flow chart of a method of determining the presence and/or associated measurements of stenotic lesions, according to some exemplary embodiments of the invention.

Reference is now made to FIG. 8, which is a simplified flow chart of a method of determining the presence and/or associated measurements of stenotic lesions, according to some exemplary embodiments of the invention.

In some embodiments of the invention, stenosis m the imaged anatomy is determined relative to a "virtually revascularized" model of the anatomy. The virtual revascularization, in some embodiments, comprises determination of a vascular tree model which removes narrowings and/or other obstructions which are determined to comprise anatomical changes due to vascular pathology.

At block 802, the flowchart starts, and each vessel segment is converted to a one-dimensional function ƒ(s) of diameter vs. distance. Optionally, the function yields vessel radius or another metric comprising information about the vessel lumen cross-section, such as area. In some embodiments, distance is obtained from the Euclidean distance formula, integrated at points along the vessel segment, for example:

$$s = \int \sqrt{dx^2 + dy^2 + dz^2}$$

where s is the integrated distance at a point along the vessel segment. The integral notation and other uses of "integration" herein should be understood as potentially approximated by summation of finite elements and/or other approximations appropriate for discrete image pixel (2-D) or voxel (3-D) samples. Additionally or alternatively, integration is potentially overa continuous, image-data derived function, for example one obtained by spline fitting and/or interpolation.

In some embodiments, the 3-D diameter of the vessel at a given point comprises an average of the diameters measured from a plurality (for example, all available) of 2-D projections visualizing that point. Optionally, the diameter is instead calculated based on the open area of the vessel, approximating the vessel lumen cross-section as circular. Optionally, the lumen cross-section area is used directly. Alternatively or additionally, radius is used. In the discussion that follows, it is to be understood that "diameter" is replaceable by another metric of lumen openness, with the method changed as necessary as would be understood by one skilled in the art making reference to the descriptions disclosed herein.

In some embodiments of the invention, an iterative process of virtual revascularization now begins for each segment (looping over each segment is not shown).

At block 804, in some embodiments, an initial reference diameter is chosen to comprise a statistical fit (for example by a linear, least mean squares method, optionally modified by a weighting function) to vessel diameter along the vessel segment length. In some embodiments, points near either end of the segment are weighted more than other segments. It should be noted that in some embodiments, determination of an unstenosed diameter at segment ends, for example, near a bifurcation, is carried out by a module specialized for bifurcation analysis, for example, as described hereinbelow in connection with FIG. 9. It should also be noted that in some embodiments, refinement of a determination of an unstenosed diameter for one or more segments is determined with reference to one or more constraints applied in consideration of a plurality of segments, for example, as described hereinbelow in connection with FIG. 10. Optionally, the point weightings are adjusted so that best-fit deviations from wider (potentially less-diseased) points along the segment are weighted as more important than deviations from narrower points. This provides a potential advantage by allowing less-diseased regions of the vessel to dominate the determination of the virtually revascularized vessel width. The weighting determinations are adjusted during subsequent revascularization operations.

At block 806, in some embodiments, differences between fit and measured points are determined, and statistics (for example, mean, standard deviation) are calculated based on the determined differences.

At block 808, in some embodiments, weighting adjustments are made, such that certain outliers from the linear fit are reduced in weight. The outliers are, for example, points which have statistically meaningful differences from the fit. Meaningful differences include, for example, being more than two standard deviations away from the best-fit line compared to the population of diameters overall.

At block 810, in some embodiments, the best fit (typically linear) is redetermined It should be noted that embodiments of the invention are not limited to a linear fit, but linearity is a convenient model for capturing the observation that vessels decrease in diameter more-or-less monotonically along their length away from the end proximal to the heart.

At block 812, in some embodiments, a test is performed to see if the best fit line has converged within some limit of stability. If not, processing continues with another fitting round at block 806. If the best fit has converged to a stable solution, processing continues with block 814.

At block 814, in some embodiments, the best fit function $\bar{f}(s)$ is used together with the original data function ƒ(s) to determine stenosis, for example:

$$\text{stenosis} = 100 * \left(1 - \frac{f(s)}{\bar{f}(s)}\right)$$

At block 816, the segment function is evaluated for additional metrics related to lesion depth, length, and position, for example, as described in connection with FIGS. 4A-4B.

For example, an output of the process, in some embodiments, comprises pairs of values s1, s2, such that for $s_1 \leq s \leq s_2$, s is within a stenotic lesion. The flowchart then ends.

Figure 9:
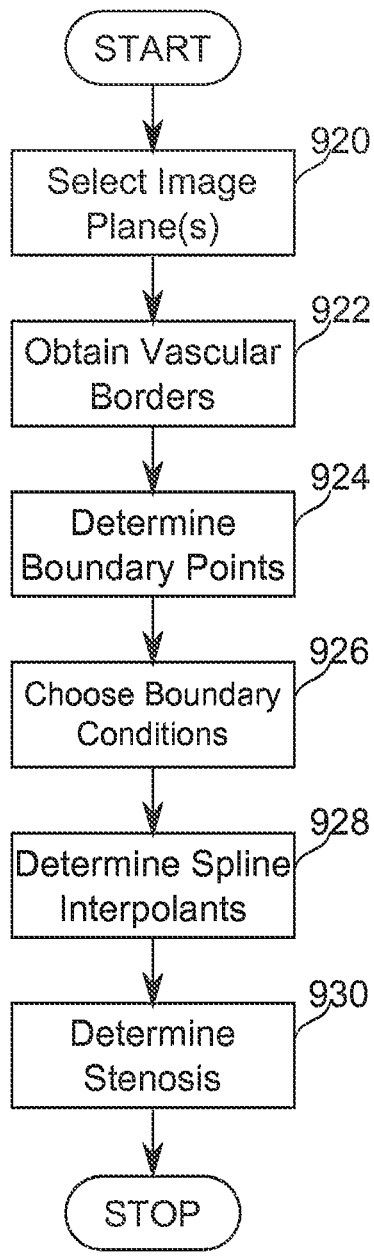
FIG. 9 is a simplified flow chart of a method of determining the presence and/or associated measurements of stenotic lesions in the region of a vessel bifurcation, according to some exemplary embodiments of the invention.

Reference is now made to FIG. 9, which is a simplified flow chart of a method of determining the presence and/or associated measurements of stenotic lesions in the region of a vessel bifurcation, according to some exemplary embodiments of the invention.

In some embodiments of the invention, diameters determined along a blood vessel segment are potentially ill-defined at a bifurcation (or trifurcation) where abrupt changes in diameter occur, or where the definition of a diameter, radius, or cross-sectional area is indeterminate. In some embodiments, a procedure is implemented whereby diameters at such boundaries are defined more clearly.

The flowchart begins, and at block 920, in some embodiments, at least one image plane passing through a bifurcation is selected as a reference plane for analysis. In some embodiments, every image plane in which a bifurcation is identified as appearing is selected during some iteration of the method. In some embodiments of the invention, determination of these image planes in turn, and/or of the region of the planes in which the bifurcation appears, proceeds from the relationship between image planes and a three-dimensionally reconstructed vascular model, generated, for example, as described in relation to FIG. 3 and in associated references given.

In some embodiments, the image section is manually selected. In some embodiments, the image plane is selected to be a plane which includes vessel center points of at least two vessels at a determined distance from the vessel (for example, 1 mm, 2 mm, 3 mm or a greater or larger distance), and a point near the center of the region of bifurcation. Optionally a different plane is selected for each pair of trunk and branch vessels (trunk and a first branch, trunk and a second branch). The method is described herein below with respect to one plane of analysis selected for one branch point vascular segment pair (a trunk and a branch), but it is to be understood that the analysis is optionally carried out on two more vascular segment pairs at a given segment junction (three, for example, in the case of a trifurcation). It is also to be understood that unstenosed diameter within more than one plane is optionally determined, and results from this plurality of determinations composed into one or more metrics describing unstenosed vascular morphology. For example, in some embodiments, a plurality of planes is selected, and an average or other statistically determined unstenosed vessel diameter selected from the set of planes analyzed. In some embodiments, unstenosed vessel widths determined in a variety of directions corresponding to different image planes are composed into an approximation of the shape of the vessel lumen circumference at different locations along its length.

At block 922, in some embodiments, for each vessel segment in a pair (for example a pair comprising a trunk vessel and a branch vessel), data sets describing each of two vessel borders (Xb,Yb) falling within a selected image plane are determined. The border data sets are, for example, determined by the locations along the vessel segment length which representing a transition from low contrast to high contrast. The transition point is determined, for example, by a threshold, a peak rate of contrast change, by a simple edge detection convolution, by a Frangi filter, or another appropriate boundary-finding method available to one skilled in the art. For convenience of exposition, the vessel border data sets (Xb,Yb) are referred to hereinbelow as the "left" border and the "right" border, it being understood that the designation of left and right in this context is potentially arbitrary.

At block 924, in some embodiments, for each of the trunk and branch segments chosen, a boundary point away from the bifurcation is chosen as a reference and/or spline interpolant termination point. The reference point may be considered as a trusted and/or anchor point, far enough from the point of a potentially lesioned bifurcation that it provides an unstenosed reference diameter for the vessel at that point. In some embodiments, the distance chosen is, for example, 1-2 mm, 2-4 mm, 1-5 mm, or another larger or smaller distance from the core of the bifurcation. In some embodiments, the distance is chosen as a function of a previously estimated vascular width, for example, 2, 3, 4 or a greater or smaller multiple of the previously estimated vascular width.

At block 926, in some embodiments, boundary conditions are determined at each of the reference points, comprising the point location. In some embodiments, a first derivative up to a derivative of order n is determined, for example by examination of border point locations from 1 to n data nodes away from the selected node point. The result, in some embodiments, is a set of four boundary conditions-two for the left wall, and two for the right; one of each wall pair being from the trunk vessel segment, and one from the branch vessel segment.

At block 928, in some embodiments, a spline interpolant is determined for each of the left and right walls which runs between the boundary conditions determined for each wall. Each such spline interpolant may be considered as an "unstenosed" border data set (xi,yi) corresponding in portions to one or the other of the original image border data sets (xb,yb) for one wall of both the trunk and branch vessel segments, and in a central portion to the region of the bifurcation. Additionally or alternatively, the left- and right-wall spline interpolants may be considered as bounding the lumen of the open or unstenosed vascular segment through the region of bifurcation.

In some embodiments, the interpolants are optimized (while preserving the boundary conditions) to maximize contrast differences across the surfaces of the interpolants. This corresponds, ideally, to adjusting the interpolant diameter to the diameter of the vascular wall, and to adjusting the interpolant center position to the center of the blood vessel. Contrast is determined, in some embodiments, by a simple edge detector, by the output of a Frangi filter, or by another means of edge detection known in the art. In some embodiments, positions within the core of the bifurcation are ignored for purposes of fit determination.

At block 930, in some embodiments, the lumen bounded by the unstenosed border data sets (Xi,Yi) is compared to the lumen bounded by the corresponding data-derived border data sets (xb,yb), to determine an absolute and/or relative degree of stenosis in the lumen comprised within the region of bifurcation. Optionally, the comparison is made, for example, after conversion of relative border locations to diameters, radii, areas, or another metric as a function of position along the vascular segment length and/or away from the region of bifurcation. Optionally, the two-dimensionally determined model is referred back to a three-dimensional model by making reference to 2-D to 3-D mappings determined during a phase of 3-D vascular tree reconstruction. Optionally, the degree of stenosis is analyzed as for stenotic regions in FIG. 8 and/or FIGS. 4A-4B. The flowchart ends.

Figure 10:
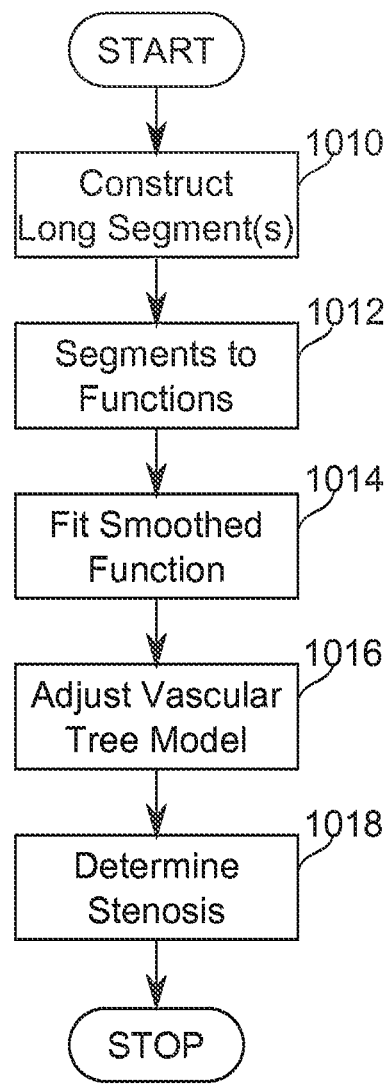
FIG. 10 is a flowchart describing in broad outline a method for refining a revascularized model of a vascular segment using information from neighbor segments, according to some exemplary embodiments of the invention.

Reference is now made to FIG. 10, which is a flowchart describing in broad outline a method for refining a revascularized model of a vascular segment using information from neighbor segments, according to some exemplary embodiments of the invention.

In some embodiments of the invention, a method is provided which takes into account constraints applicable to the morphometric relationships between vascular segments in determining an unstenosed vascular model. Potentially, this allows more accurate determination of an unstenosed vascular model, and/or reduces the occurrence of artifacts which do not reflect reasonable anatomical situations.

The flowchart begins, and at block 1010, one or more long segments are constructed by the concatenation of a plurality of interconnected shorter segments into single functions. In some embodiments, the shorter segments are defined by branch points, and the construction of long segments comprises trimming off different branch alternatives for different long segments. In some embodiments, each possible long segment implied by the underlying vessel segment hierarchy is constructed.

At block 1012, in some embodiments, long segments are converted to functions, for example, to a one dimensional function of arc-length. In some embodiments of the invention, the function describes radius, diameter, cross-sectional area, and/or another metric related to a degree of stenosis as a function of position along the segment.

At block 1014, in some embodiments, a smoothed function {hacek over (f)}(s) is fitted to the data off(s). The fitting, in some embodiments, is subject to a similarity criterion, for example, minimization of ƒ(s)-{hacek over(0)}}(s)I. The fitting, in some embodiments, is subject to a smoothness criterion, for example, minimization of I{hacek over (J)}"(s).

In some embodiments, the fitting further comprises the criterion of minimizing {hacek over (f)}}'(s), for example, such that this value is everywhere non-positive. A potential advantage of this criterion is that it takes advantage of an observed property of healthy vascular trees, which are seen to narrow monotonically when moving from trunk to branch. Thus, for example, a case may arise in which an entire segment is narrowed, thus providing no healthy region as an internal reference. In such a case, a single undiseased downstream segment nevertheless potentially signals that the unstenosed diameter of the highly diseased upstream segment should be larger than the observed vessel diameter.

At block 1016, in some embodiments, an adjusted unstenosed model of a vascular segment is referred back to the original vascular tree model.

At block 1018, in some embodiments, a degree of stenosis is calculated from the adjusted unstenosed vascular segments, for example as described herein above with reference to FIG. 8 and/or FIGS. 4A-4B. The flowchart ends.

Total Occlusion and Thrombus

In some embodiments, features which connect vessel walls and/or comprise non-vascular inclusions within the vessel walls are determined by processing of images and/or of the reconstructed vasculature.

In some embodiments of the invention, a total occlusion of the vasculature is identified, for example, by an abrupt border between lumen and background intensities, for example, a complete break in the continuity of blood-borne contrast agent imaged along a blood vessel in the image data. In some embodiments, the occlusion is determinable to be associated or not associated with bridging (shunting) vessels. In some embodiments, bridging vessels are distinguishable from the main artery by, for example, an increase in tortuosity, a decrease in vessel diameter, and/or a sharp change in vessel direction.

In some embodiments, one or both occlusion boundaries (proximal/distal) are characterized by the morphology of one or more occlusion/lumen boundaries. For example, a degree of boundary curvature may be assessed by a parabolic fit, a spline fit, or another fitting function. In some embodiments, an occlusion morphology is determined by a relative position of predefined points along the occlusion curve (for example, center-most point, compared in longitudinal position to points within some radius percentage of the vessel wall), or another characterizing feature of the occlusion morphology.

In some embodiments, thrombotic structures in the vasculature are determinable from the presence of certain relatively contrast agent-free, potentially ovoid or spherical regions within the lumen of a blood vessel. In some embodiments, a vessel cross-section potentially containing a thrombus is identified by region comprising a sharp drop in contrast agent density, visible as an increase in brightness in some imaging modalities, or otherwise distinguishable from its surroundings. The region in the cross-section is potentially surrounded by a region of differing (for example, higher) contrast density. In some embodiments, vessel inclusions are identified, for example, by a ratio of free (unconnected to a wall) surface area, free circumference, and/or free angular arc to a wall-connected portion of the inclusion. In some embodiments, vessel inclusions such as thrombi are identified by being unconnected to a vessel wall on at least three sides.

Determination of Other Metrics

In some embodiments of the invention, metrics for conversion into VSST parameters are determined from the three- or two-dimensional reconstruction of the vasculature.

In some embodiments, metrics such as numbers and order of branching points are determined from the branch points determined during vascular reconstruction.

In some embodiments, metrics such as the size of the lesion, arc-distances from nearby bifurcations (points marked "Bifurcation location" in FIG. 4A), and/or distances between adjacent lesions are determined from the vascular reconstruction. In some embodiments, the radius, curvature and/or tortuosity of vessels is extracted along the tree from the vascular reconstruction.

In some embodiments, metrics comprising distances between reference points on the vessel (for example, lesion lengths, relative positions, and/or segment lengths) can be determined by integrating distance over the length of a segment arc. This may be, for example, according to integrated length in three dimensions:

$$s = \int \sqrt{dx^2 + dy^2 + dz^2}$$

where s is the total distance traversed.

In some embodiments, a metric comprising a measure of vessel segment tortuosity is determined by integrating on angular deviations along a segment length.

In some embodiments, where bifurcations have been identified during the phase of artery tree construction, lesions near the bifurcations are classified according to the Medina classification of bifurcation lesion analysis.

In some embodiments, metrics comprising absolute measurements of vessel diameter are obtained from the 2D and/or 3D vessel data, for example, by making measurements perpendicular to segment direction along the vascular tree.

Conversion of Metrics into VSST Parameters

In some embodiments of the invention, one or more VSST parameters are referred to a specific, anatomically identified vessel segment as part of the scoring procedure. In some embodiments, vessel segments are automatically identified by registration of the vessel segment tree to an atlas comprising one or more standard vascular morphology patterns. In some embodiments, the determination is automatic and unguided, for example by finding a best fit pattern between the atlas and the acquired image data.

In some embodiments, deviations from an atlas standard (for example, due to increases in tortuosity, total occlusions, and/or development of shunting vessels) are identified. In some embodiments, a vascular identification of a segment comprising one or more metrics which deviate significantly from an atlas standard value is identified as such for an operator or otherwise flagged as uncertain. For example, a vessel which is longer, of a different width, or more tortuous than a corresponding atlas standard segment may be flagged according to a threshold of 50%, 100%, or another percentage of difference. Additionally or alternatively, the segment may be flagged according to a statistically unlikely (P<0.05, P<0.001, or less than some other P value) morphology.

In some embodiments, identification is partially guided, for example by prompting an operator to identify one or more vascular segments, and then automatically identifying remaining vessels by their relative position in space and/or along branch points. In some embodiments of the invention, automatic determination is displayed for potential correction by an operator through a computer user interface. In some embodiments, vascular segments where a lesion has been detected are presented to an operator for manual identification. [0196] In some embodiments of the invention, composition of metrics into VSST parameters/subscores proceeds from determined metrics according to the specific requirements of the VSST. In the SYNTAX Score method, for example, a question requests determining which of left or right dominance (two distinctive anatomical patterns) applies to the vasculature being evaluated. In some embodiments, the parameter corresponding to this question is determined from automatic inspection of vascular branching point number and order metrics.

In some embodiments of the invention, one or more VSST questions concerns occlusive degree, vessel diameter and/or relative locations of stenotic lesions detected in received image data. In some embodiments of the invention, one or more parameters describing the number and extent of lesions are composed by applying thresholds based on criteria supplied for a VSST to vascular metric data. For example, in a SYNTAX Score evaluation, a coronary lesion is counted when it meets criteria of vessel diameter being at least 1.5 mm, and a level of stenosis being at least 50%. Also for example, relative positions of lesions are relevant to the scoring of a lesion as one or two lesions. Optionally, for example in SYNTAX Score, an inter-occlusion distance threshold for scoring as one or two lesions is a function of vessel diameter, for example three vessel diameters. In some embodiments, the number of segments that a lesion comprises is scored.

In some embodiments, one or more VSST questions concerns the presence of a total occlusion, its curve morphology, depth, and/or position relative to nearby branch points. In some embodiments, a parameter describing the presence of shunting ("bridging") vessels around a total occlusion is determined, for example, from one or metrics describing an abrupt change in vessel diameter, vessel direction, and/or vessel tortuosity.

In some embodiments, one or more VSST questions requests an abstracted description of tortuosity, which is extracted from determined metrics. For example, a tortuosity metric may comprise a quantified description of integrated tortuosity along a segment. The tortuosity parameter in the case of a SYNTAX Score, for example, requests counting "One or more bends of 900 or more, or three or more bends of 45° to 90° proximal of the diseased segment" (www(DOT)syntaxscore(DOT)com). This parameter may be abstracted from a tortuosity metric by, for example, integrating accumulated curvature, and counting the number of curves which reach each threshold criterion.

In some embodiments of the invention, the VSST parameter description of a lesion occlusion may be more specific than "more than 50% occlusion". For example, a SYNTAX Score requests: "Estimation of the length of that portion of the stenosis that has 2:50% reduction in luminal diameter in the projection where the lesion appears to be the longest" (www(DOT)syntaxscore(DOT)com). In some embodiments, occlusion is separately determined as a metric along two or more planes to which the lesion is projected. In some such embodiments, the parameter determination uses the occlusion length in the plane for which the lesion is longest. In some embodiments, (for example, with stenosis opener modeling) occlusion is determinable across any radial direction along the segment axis, continuously, or at any number of discrete radial directions. In some embodiments, conversion of a length to a parameter comprises determining if a length (such as a lesion length) meets a threshold criterion, for example, a SYNTAX Score distinguishes lesions more than 20 mm long. In another VSST, the length is optionally longer or shorter, as specified.

In some embodiments of the invention, a VSST parameter may comprise temporal information about a lesion. For example, in a SYNTAX Score parameter, "multiple persisting opacifications" (www(DOT)syntaxscore(DOT)com) along a vascular wall appearing before the injection of contrast agent are potentially scored as "heavy calcification". In some embodiments of the invention, temporal information from an angiogram or other time-resolved image set is converted to a VSST parameter. In some embodiments, regions of opacity imaged along vessel segments before contrast agent injection are mapped to the full vascular tree by image feature alignment or by another matching algorithm. In some embodiments, an appropriate threshold function is previously determined such that a given total extent and/or number of pre-contrast agent opacities are determined to be "multiple persisting opacifications"; the parameter is determined based on said threshold function.

In some embodiments of the invention, a VSST parameter comprises a determination of the presence of a thrombus. The SYNTAX Score, for example, defines a thrombus as a lucency meeting a complex, informally described list of criteria: "Spheric, ovoid or irregular intraluminal filling defect or lucency surrounded on three sides by contrast medium seen just distal or within the coronary stenosis in multiple projections or a visible embolization of intraluminal material downstream" (www(DOT)syntaxscore(DOT)com). In some embodiments of the invention, thrombi are identified, for example, by a run of "thrombus cross-sections" terminated on at least one side by contrast running across the full width of the vessel. In some embodiments the thrombus is identified as an inclusion during vessel reconstruction. In some embodiments of the invention, a library of image examples wherein a thrombus has been identified by specialist grading is used to train a machine learning algorithm (for example, a neural network, Bayesian model, or other variably weighted algorithm) for the identification of gradients and intensity statistics typical for thrombi, as well as prior probabilities on shape characteristics, facilitating a correct classification and identification of a thrombus in the image.

In some embodiments of the invention, a VSST parameter comprises a determination of diffuse disease. The SYNTAX Score, for example, defines diffuse disease as "Present when at least 75% of the length of any segment(s) proximal to the lesion, at the site of the lesion or distal to the lesion has a vessel diameter of <2 mm." In some embodiments of the invention, the metrics comprising vessel diameters are automatically inspected relative to one or more identified lesion sites, and evaluated for meeting the criterion of diameter (for example, <2 mm), and/or total relative length meeting this criterion (for example 75%). It should be understood that the criteria chosen can be altered to fit the criteria of the VSST; the examples given are not limiting.

Examples hereinabove describe the conversion of automatically determined vascular tree metrics into VSST parameters, which are typically described in natural language originally targeted for application to non-automatic determination. The progression from image data, to automatically determined morphological metrics to automatically determined VSST parameter comprises distinctive stages in vascular state score determination which are not present as such or by implication in a VSST such as SYNTAX Score.

Some of the examples herein above are described with particular reference to parameters of the SYNTAX Score method. These examples illustrate to someone skilled in the art a range of methods-comprised in some embodiments of the invention-which are applicable, suitably modified, to other VSST parameters. For example, specific category-determining values (threshold values in particular) are readily modified. Also, it may be readily seen by someone skilled in the art that further compositions into VSST parameters of metrics including vascular anatomy distances, lengths, diameters, connectivities, tortuosities, and/or angles are obtainable based on the principles described hereinabove, to comprise embodiments of the present invention.

In some embodiments of the invention, one or more VSST parameters covering substantially the same morphometric determination are calculated. A VSST, such as the SYNTAX Score, which is originally targeted for manual determination, will often comprise questions which elicit a response having a limited range of values, often binary-presence or absence of a lesion, for example. Nevertheless, an automatic parameter determination often arrives at a final yes/no parameter value after first calculating a value in some continuous, or at least multi-valued range. Some embodiments of the invention make available both the formal VSST parameter value and one or more quantified results from which it was directly taken. This is a potential advantage, for example, to provide finer granularity for evaluation during later refinement of the recommendations made from a VSST score result, and/or for refinement of the VSST scoring method itself For example, an occlusion score which in a VSST score is formally cut off at 50% occlusion=! point, might be found upon further analysis to be more predictive if a range of occlusions (for example, 40-60% occlusion) were mapped to a corresponding range of partial point values.

It should be noted that embodiments of the present invention are not limited to entirely automatic production of all subscores of a given VSST score. Some embodiments of the invention comprise functionality that works together with data provided by other means for determining VSST parameters. In some embodiments of the invention, for example, parameters representing flow function, patient history, and/or other clinical data, are also converted into subscores for composition into a VSST score. In some embodiments, manual and automatic scoring relate interactively, for example to improve accuracy of results and/or provide assurance to a practitioner that the automatic scoring for a given case is generally accurate.

Composition of VSST Parameters into a Vascular State Score

Figure 6:
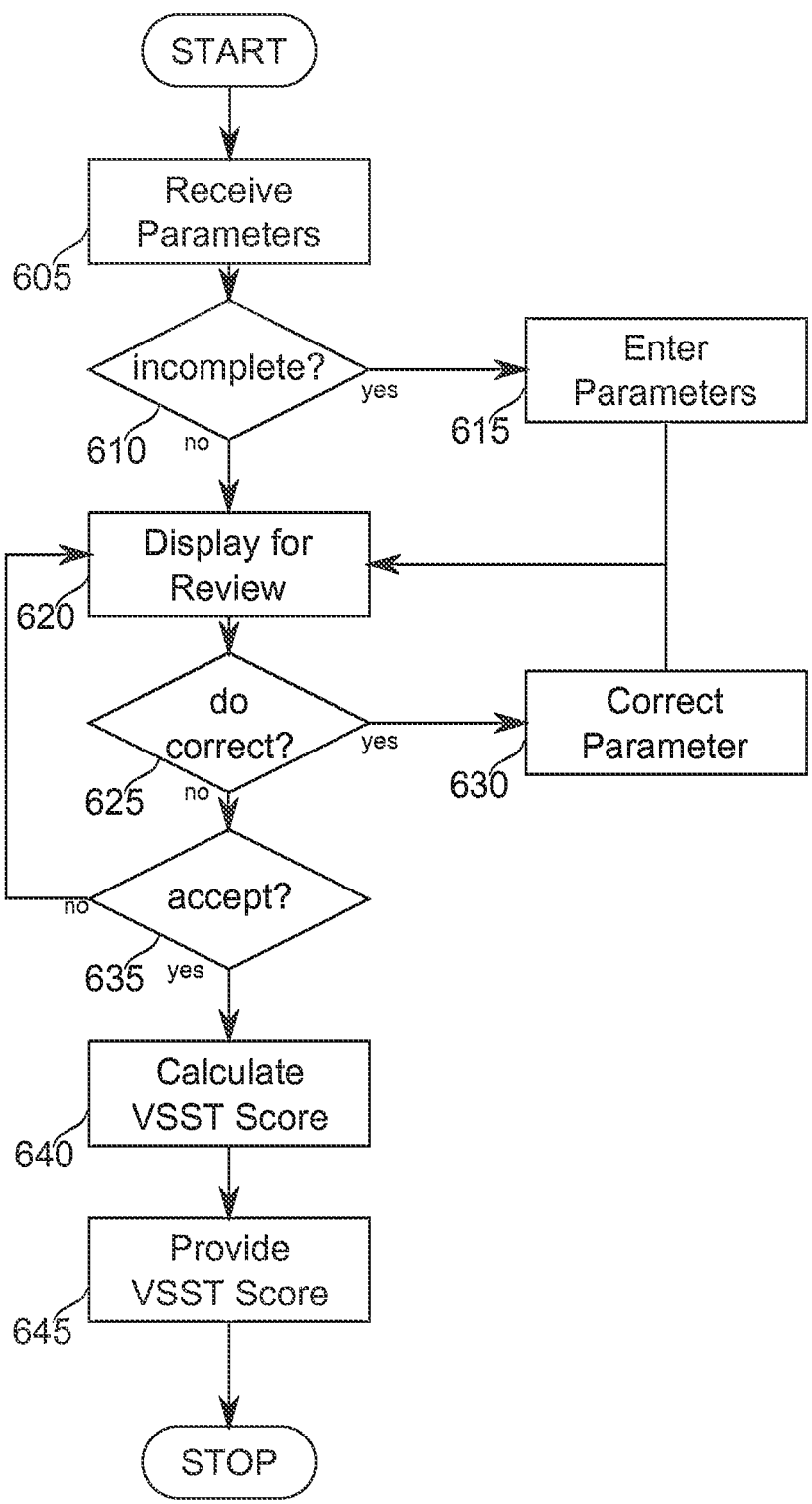
FIG. 6 is a simplified flow chart describing in outline an exemplary vascular state score determination from automatically calculated parameter values, according to some exemplary embodiments of the invention.

Reference is now made to FIG. 6, which is a simplified flow chart describing in outline an exemplary vascular state score determination from automatically calculated parameter values, according to some exemplary embodiments of the invention.

At block 605, the flow chart starts, and, in some embodiments of the invention, one or more parameters automatically determined from an image dataset is received by a vascular scoring module.

In some embodiments, provision is made for the manual entry of parameter values, and/or correction by feedback of automatically determined values.

At block 610, in some embodiments, a determination is made whether or not the provided data is complete, or needs manual completion. If not, the flowchart continues at block 620. Otherwise, the flowchart continues at block 615.

At block 615, in some embodiments, the operator is prompted to supply missing data. The data may be, for example, ordinary clinical data such as patient vital statistics. In some embodiments, the operator input may be to supply vessel identifications. In some embodiments, one or more image-based parameters not supported by the specific embodiment of the invention is prompted for.

At block 620, in some embodiments, the operator is provided, through a user interface (such as a graphical user interface [GUI]), with the opportunity to review and/or correct parameter determinations made automatically and/or manually. In some embodiments of the invention, automatic parameter determinations are presented together with an automatically evaluated indication of confidence in parameter correctness. Such an indication may be calculated, for example, based on image signal-to-noise, the complexity of the anatomy encountered, the quality of matching of an anatomical reconstruction to a standard atlas, and/or other issues encountered during image processing which potentially indicate reduced confidence in the quality of an automatically determined result.

At block 625, in some embodiments, a determination is made for the issuance of a "correction" event (issued, for example, from the user interface). If there is such an event, the correction is made at block 630 in some embodiments, optionally using additional interface elements and/or another interface mode such as a dialog, and the method continues at block 620. Otherwise, flow continues to block 635.

At block 635, in some embodiments, a determination is made for the issuance of an "accept" event (issued, for example, from the user interface). If this event is not yet issued, flow returns to block 620. Otherwise, the parameters are passed to the vascular state calculator module and the VSST score (for example, SYNTAX Score outcome) is calculated at block 640 in some embodiments, according to the specifications of the VSST. The VSST may specify, for example, a parameter weighting such that the parameters, composed for the score, are reduced a single numeric score. In some embodiments of the invention, parameters automatically or manually flagged as uncertain are taken into account, and a range of weighted scores provided based on possible alternative values for the weighted parameters. In some embodiments, a single value of the range is highlighted as a best estimate of the VSST score for the provided image data.

It should be noted that a VSST score, in some embodiments, reduces to a recommendation to take one of a small number of alternative treatment actions, for example, one of two actions. In the case of a SYNTAX Score, for example, the decision at stake is a choice between PCI and CABG. Thus, the exact or "true" SYNTAX Score is potentially less important than consistency of results. Furthermore, the potentially most-likely cases wherein vascular anatomy is sufficiently abnormal as to cause uncertainty for automatic determination are those with the most disease complexity. Accordingly, uncertainty of an automatically determined SYNTAX Score itself potentially comprises an indication of vascular state.

At block 645, the VSST score is provided at an output (for example, to a user interface and/or a medical records database server), and the flowchart ends.

It should be noted that the above-described flowchart is for the purposes of illustration, and that the actual ordering and branching of operations may be different without change to the essentials of the method. For example, in some embodiments, the VSST score is obtained not only at the end of the procedure, but also updated upon initial parameter receipt, and upon each change to the parameter data. In some embodiments, one or more stages of user interaction (for example, blocks 615-635) are removed or streamlined In some embodiments, all image-based VSST score parameters are automatically determined In some embodiments, all VSST score parameters are automatically determined and/or obtained, for example, from a database comprising the patient's medical records.

It is expected that during the life of a patent maturing from this application many relevant vascular state scoring tools (VSSTs) will be developed and the scope of the term VSST is intended to include all such new technologies a priori.

As used herein the term "about" refers to 10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Andriotis A, et al., "A new method of three-dimensional coronary artery reconstruction from x-ray angiography: validation against a virtual phantom and multislice computed tomography". Catheter Cardiovasc Interv 71 (2008) 28-43.

Kappetein A P et al., "Current percutaneous coronary intervention and coronary artery bypass grafting practices for three-vessel and left main coronary artery disease. Insights from the SYNTAX run-in phase". European Journal of Cardio-thoracic Surgery 29 (2006) 486-491.

Pellot C et al., "A 3D reconstruction of vascular structures from two X-ray angiograms using an adapted simulated annealing algorithm". IEEE Trans Med Imaging 13 (1994) 48-60.

Sprague K et al., "Coronary x-ray angiographic reconstruction and image orientation". Med Phys 33 (2006) 707.

Youssef G and Budoff M. "Role of computed tomography coronary angiography in the detection of vulnerable plaque, where does it stand among others?" Angiol 1 (2013) 111.

The invention is claimed as follows:

1. An apparatus for coronary artery disease scoring, the apparatus comprising: a processor; and
a memory storing non-transitory computer-readable instructions, which when executed, cause the processor to:
access a computerized model representative of vascular segments of a patient, wherein the computerized model comprises one or more stenosed vascular segments and a plurality of normal vascular segments and,
generate an unstenosed computerized model based on virtually enlarging the plurality of stenosed vascular segments of the computerized model based on widths of the plurality of normal vascular segments,
determine, based on the computerized model and the unstenosed computerized model, metrics associated with one or more vascular locations along the enlarged plurality of stenosed vascular segments, wherein the metrics include (1) a number of branching points, (2) geometry information associated with individual aspects of the vascular locations, and (3) tortuosity of the vascular locations,
determine, based on blood flow parameters of the computerized model and the unstenosed computerized model, a severity for at least one of the one or more stenosed vascular segments, and cause a user interface to display the severity of the at least one stenosed vascular segment and stenosis information, wherein the stenosis information is based on conversion of the metrics to one or more vascular state scores.

2. The apparatus of claim 1, wherein the one or more vascular locations correspond to lesions.

3. The apparatus of claim 1, wherein the vascular state scores address vascular state questions including one or more of occlusive degree, vessel diameter of lesions, and presence of a total occlusion.

4. The apparatus of claim 1, wherein the vascular state scores include a parameter describing presence of shunting around a total occlusion, and wherein the parameter is determined based on the metric describing the geometry information.

5. The apparatus of claim 1, wherein the vascular state scores are binary values that answer vascular state scoring questions.

6. The apparatus of claim 1, wherein a first vascular state score indicates a size of a lesion and a second vascular state score indicates a distance of the lesion from a branch point, and wherein a total vascular state score is calculated based on a combination of the first vascular state score and the second vascular state score.

7. The apparatus of claim 6, wherein a severity of stenosis is displayed via the user interface in conjunctive with the total vascular state score.

8. The apparatus of claim 1, wherein the unstenosed computerized model is generated according to a weighting function, wherein vascular segments of the unstenosed computerized model with widths below vascular segment widths of the unstenosed computerized model are weighted more heavily than vascular segments of the unstenosed computerized model with widths above the vascular segment widths of the unstenosed computerized model.

9. A method implemented by a system of one or more processors, the method comprising:
   accessing a computerized model representative of vascular segments of a patient, wherein the computerized model comprises one or more stenosed vascular segments and a plurality of normal vascular segments,
   generating an unstenosed computerized model based on virtually enlarging the plurality of stenosed vascular segments of the computerized model based on widths of the plurality of normal vascular segments,
   determining, based on the computerized model and the unstenosed computerized model, metrics associated with one or more vascular locations along the enlarged plurality of stenosed vascular segments, wherein the metrics include (1) a number of branching points, (2) geometry information associated with individual aspects of the vascular locations, and (3) tortuosity of the vascular locations,
   determining, based on blood flow parameters of the computerized model and the unstenosed computerized model, a severity for at least one of the one or more stenosed vascular segments, and
   causing a user interface to display the severity of the at least one stenosed vascular segment and stenosis information, wherein the stenosis information is based on conversion of the metrics to one or more vascular state scores.

10. The method of claim 9, wherein the one or more vascular locations correspond to lesions.

11. The method of claim 9, wherein the vascular state scores address vascular state questions including one or more of occlusive degree, vessel diameter of lesions, and presence of a total occlusion.

12. The method of claim 9, wherein the vascular state scores include a parameter describing presence of shunting around a total occlusion, and wherein the parameter is determined based on the metric describing the geometry information.

13. The method of claim 9, wherein the vascular state scores are binary values that answer vascular state scoring questions.

14. The method of claim 9, wherein a first vascular state score indicates a size of a lesion and a second vascular state score indicates a distance of the lesion from a branch point, and wherein a total vascular state score is calculated based on a combination of the first vascular state score and the second vascular state score.

15. Method of claim 14, wherein a severity of stenosis is displayed via the user interface in conjunctive with the total vascular state score.

16. Non-transitory computer storage media storing instructions that when executed by a system of one or more processors cause the one or more processors to:
   access a computerized model representative of vascular segments of a patient, wherein the computerized model comprises one or more stenosed vascular segments and a plurality of normal vascular segments and,
   generate an unstenosed computerized model based on virtually enlarging the enlarged plurality of stenosed vascular segments of the computerized model based on widths of the plurality of normal vascular segments,
   determine, based on the computerized model and the unstenosed computerized model, metrics associated with one or more vascular locations along the vascular segments, wherein the metrics include (1) a number of branching points, (2) geometry information associated with individual aspects of the vascular locations, and (3) tortuosity of the vascular locations,
   determine, based on blood flow parameters of the computerized model and the unstenosed computerized model, a severity for at least one of the one or more stenosed vascular segments, and cause a user interface to display the severity of the at least one stenosed vascular segments and stenosis information, wherein the stenosis information is based on conversion of the metrics to one or more vascular state scores.

17. The computer storage media of claim 16, wherein the one or more vascular locations correspond to lesions.

18. The computer storage media of claim 16, wherein the vascular state scores address vascular state questions including one or more of occlusive degree, vessel diameter of lesions, and presence of a total occlusion.

19. The computer storage media of claim 16, wherein the vascular state scores include a parameter describing presence of shunting around a total occlusion, and wherein the parameter is determined based on the metric describing the geometry information.

20. The computer storage media of claim 16, wherein the vascular state scores are binary values that answer vascular state scoring questions.

21. The computer storage media of claim 16, wherein a first vascular state score indicates a size of a lesion and a second vascular state score indicates a distance of the lesion from a branch point, wherein a total vascular state score is calculated based on a combination of the first vascular state score and the second vascular state score, and wherein a severity of stenosis is displayed via the user interface in conjunctive with the total vascular state score.

* * * * *